(12) United States Patent
Mizumoto et al.

(10) Patent No.: US 8,967,459 B2
(45) Date of Patent: Mar. 3, 2015

(54) ANALYZER AND METHOD OF ANALYZING

(71) Applicant: Sysmex Corporation, Kobe-shi, Hyogo (JP)

(72) Inventors: Toru Mizumoto, Kobe (JP); Fumio Inoue, Kobe (JP)

(73) Assignee: Sysmex Corporation, Kobe (JP)

(*) Notice: Subject to any disclaimer, the term of this patent is extended or adjusted under 35 U.S.C. 154(b) by 0 days.

(21) Appl. No.: 13/911,897

(22) Filed: Jun. 6, 2013

(65) Prior Publication Data

US 2013/0292464 A1 Nov. 7, 2013

Related U.S. Application Data

(63) Continuation of application No. 13/247,298, filed on Sep. 28, 2011, now Pat. No. 8,474,692.

(30) Foreign Application Priority Data

Sep. 29, 2010 (JP) .................. 2010-219110

(51) Int. Cl.
G01N 35/00 (2006.01)

(52) U.S. Cl.
CPC .... G01N 35/00732 (2013.01); G01N 35/00663 (2013.01)
USPC ...................................... 235/375

(58) Field of Classification Search
USPC ...................................... 235/375
See application file for complete search history.

(56) References Cited

U.S. PATENT DOCUMENTS

| | | | |
|---|---|---|---|
| 5,972,295 A | 10/1999 | Hanawa et al. | |
| 7,561,724 B2 | 7/2009 | Chung et al. | |
| 2004/0102997 A1* | 5/2004 | Kikuchi et al. | 705/1 |
| 2007/0198213 A1 | 8/2007 | Parvin et al. | |
| 2009/0074618 A1 | 3/2009 | Mizumoto et al. | |
| 2010/0140341 A1 | 6/2010 | Kuo et al. | |

FOREIGN PATENT DOCUMENTS

| | | |
|---|---|---|
| CN | 101358987 A | 2/2009 |
| CN | 101387649 A | 3/2009 |
| JP | 2003-248005 A | 9/2003 |
| JP | 2007-333466 A | 12/2007 |
| JP | 2009-068979 A | 4/2009 |
| JP | 2012-510621 A | 5/2012 |
| WO | WO 2010/063141 A1 | 10/2010 |

OTHER PUBLICATIONS

Office Action, and English language translation thereof, in corresponding Chinese Application No. 201110290147.5, dated Jun. 5, 2013, 24 pages.

* cited by examiner

Primary Examiner — Thien M Le
Assistant Examiner — Toan Ly
(74) Attorney, Agent, or Firm — Brinks Gilson & Lione

(57) ABSTRACT

An analyzer which analyzes an analyte by using the analyte and consumables, the analyzer comprising: an automatic reading device which reads a first product information related to a consumable via an identifier given to the consumable or a container containing the consumable; and a controller which permits an analysis operation when the first product information is suitable information read by the automatic reading device via the identifier, and prompts an operator to manually enter a second product information comprising information specifying the manufacturer or seller of the consumable when the automatic reading device cannot read the identifier or the information read via the identifier is not suitable as the first product information and permits the analysis operation and storage of the input second product information when the operator has entered the second product information.

20 Claims, 22 Drawing Sheets

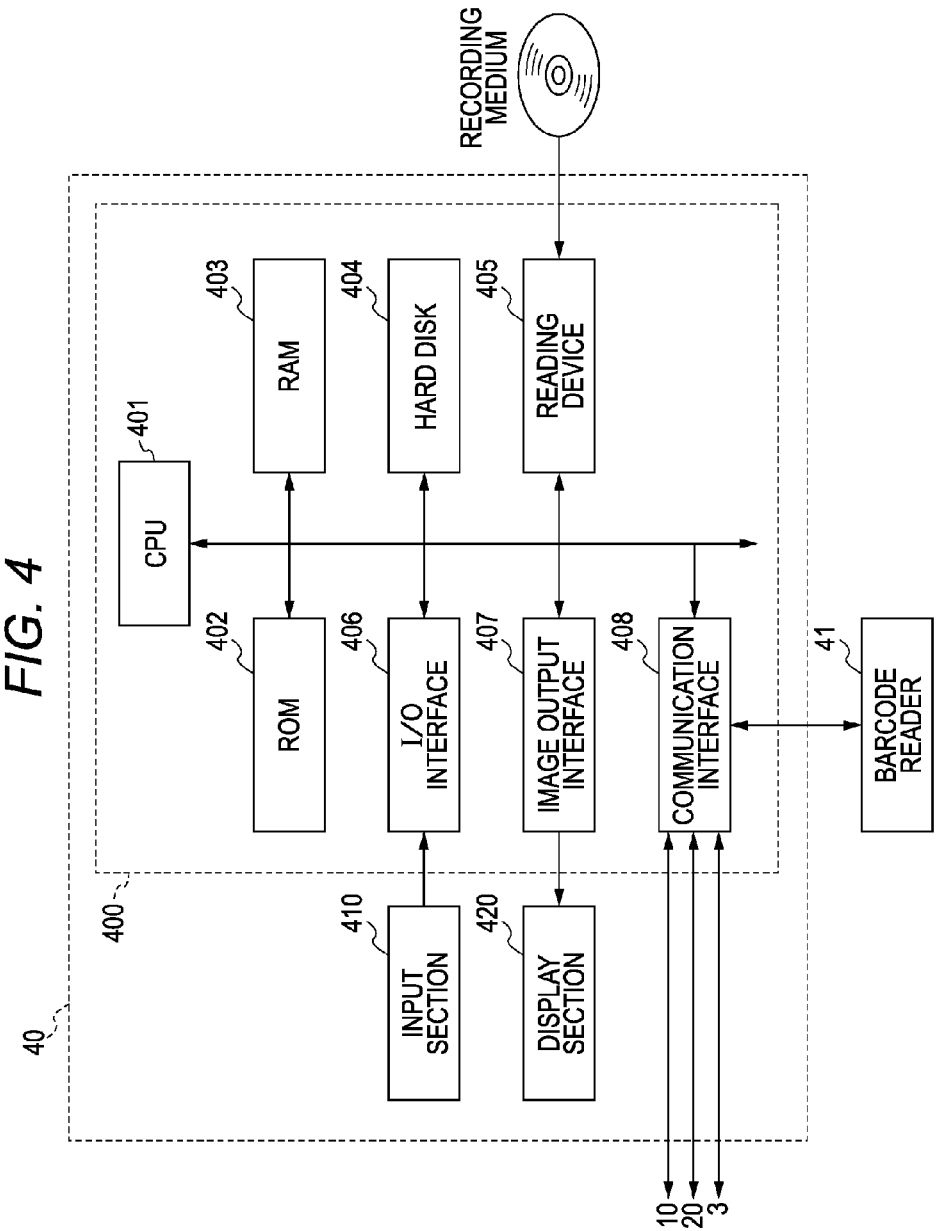

FIG. 5

| REPLACEMENT DATE | REPLACEMENT TIME | LOGIN NAME | CONSUMABLE TYPE | LOT No. | EXPIRATION DATE | PRODUCT CODE | MANUFACTURER | MANUFACTURER ADDRESS |
|---|---|---|---|---|---|---|---|---|
| 2010/07/01 | 09:06:00 | max | DILUTION LIQUID A | A2010 | 2010/08/01 | UUU-900 | ABCD CORPORATION | XX CITY ···· |
| 2010/07/01 | 09:16:00 | max | STAIN LIQUID A | A2010 | 2010/08/01 | | | |
| 2010/07/01 | 09:26:00 | max | DILUTION LIQUID B | A2010 | 2010/08/01 | | | |
| 2010/07/01 | 09:36:00 | max | STAIN LIQUID B | A2010 | 2010/08/01 | | | |
| 2010/07/01 | 09:46:00 | max | SHEATH LIQUID | A2010 | 2010/08/01 | | | |
| 2010/07/04 | 09:06:00 | max | DILUTION LIQUID A | A2010 | 2010/08/01 | | | |
| 2010/07/04 | 09:16:00 | max | STAIN LIQUID A | A2010 | 2010/08/01 | | | |
| 2010/07/04 | 09:26:00 | max | DILUTION LIQUID B | A2010 | 2010/08/01 | | | |
| 2010/07/04 | 09:36:00 | max | STAIN LIQUID B | A2010 | 2010/08/01 | | | |
| 2010/07/04 | 09:46:00 | max | SHEATH LIQUID | A2010 | 2010/08/01 | | | |

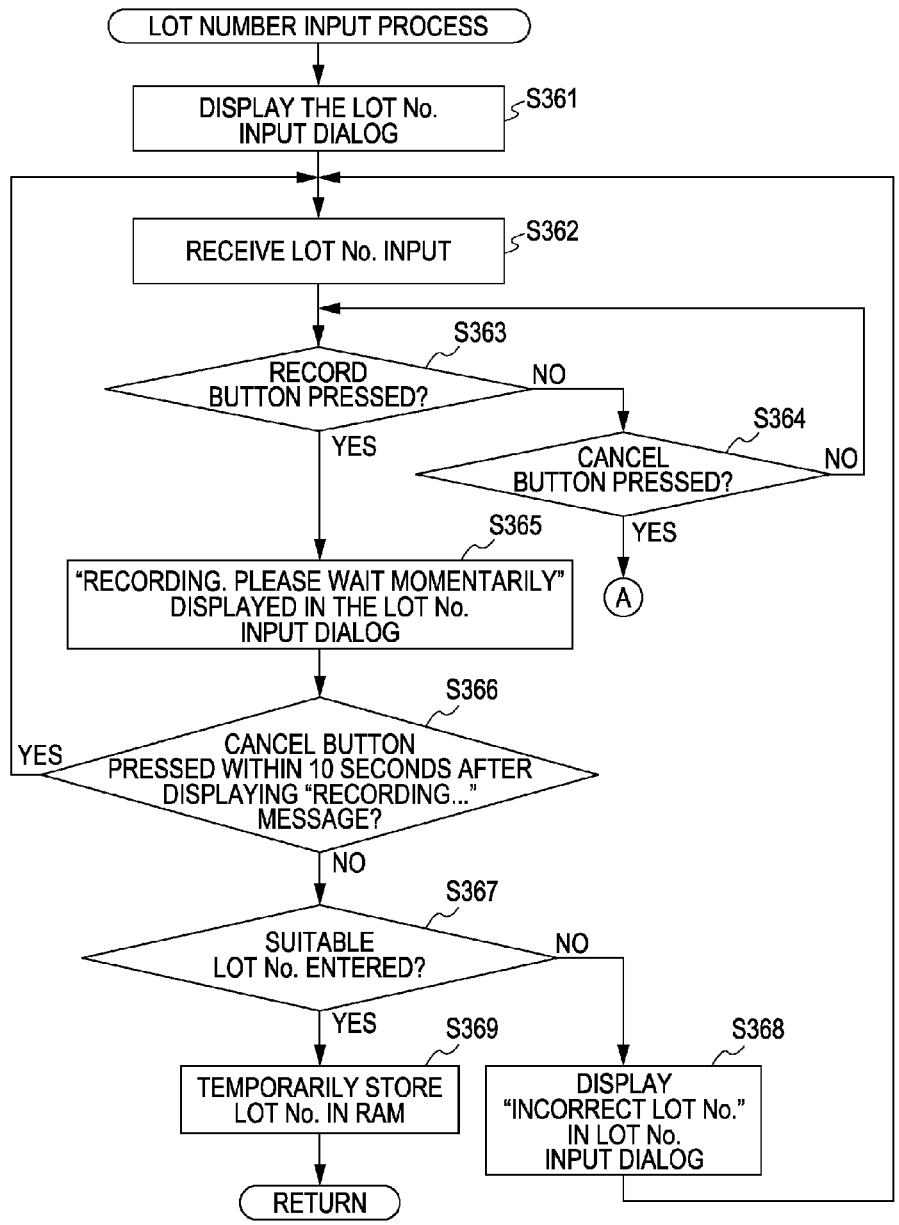

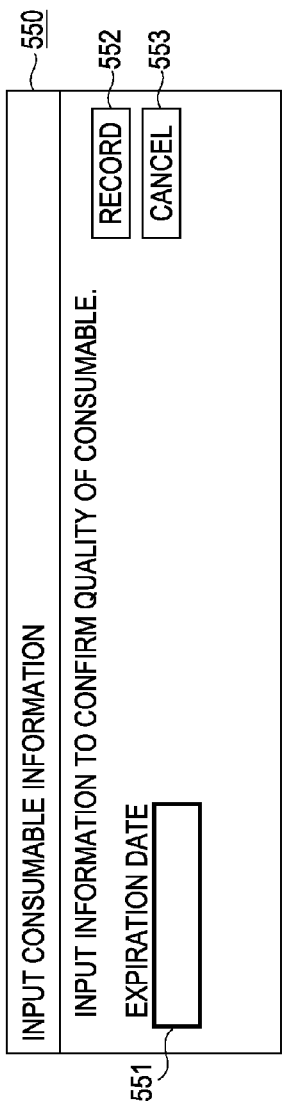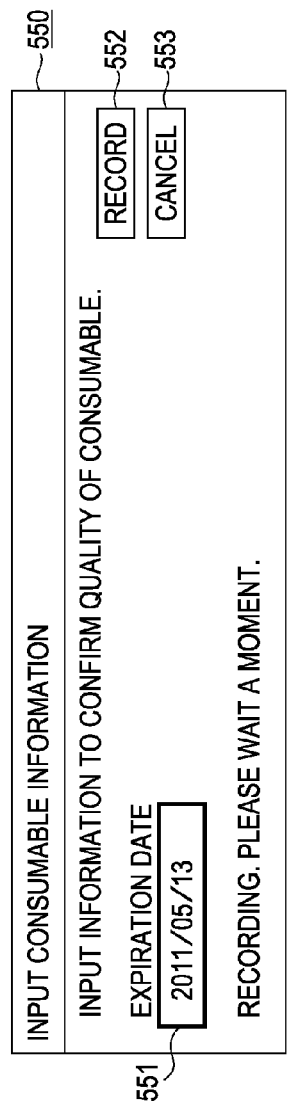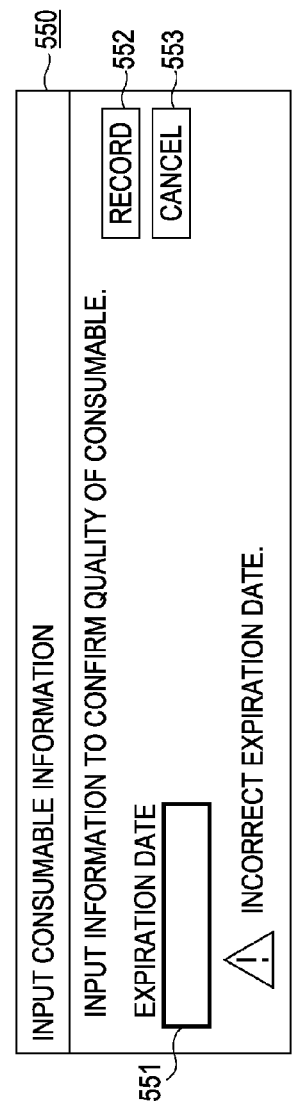

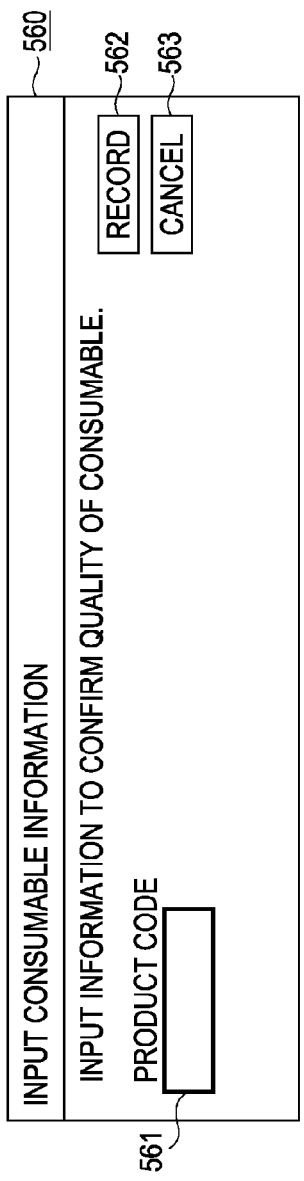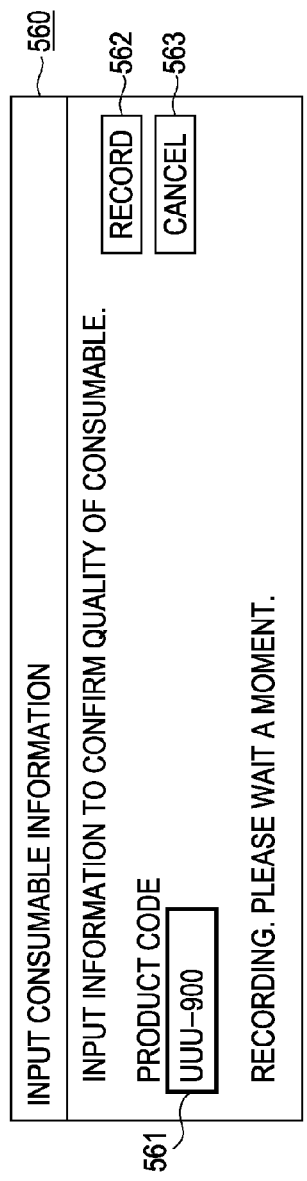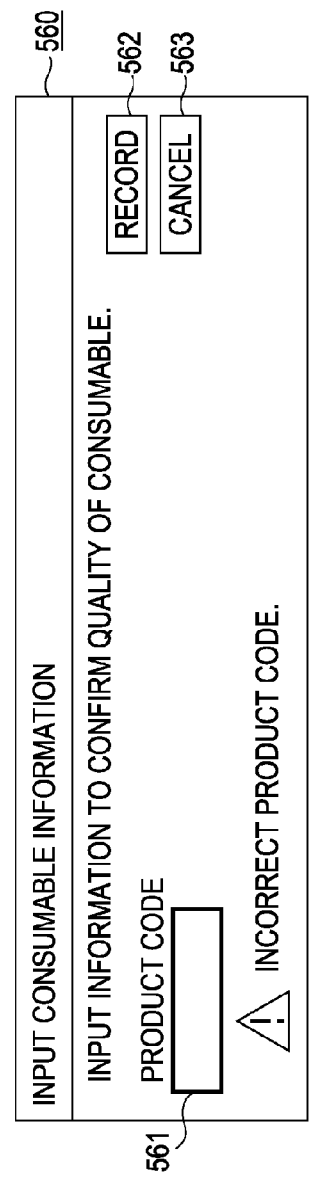

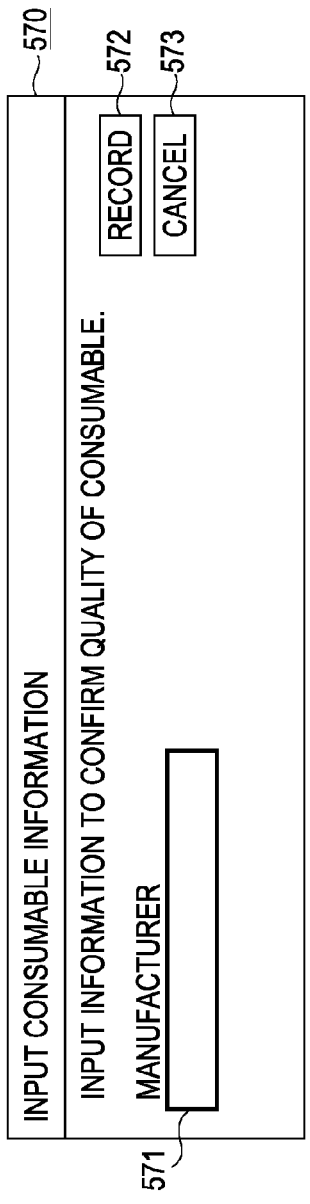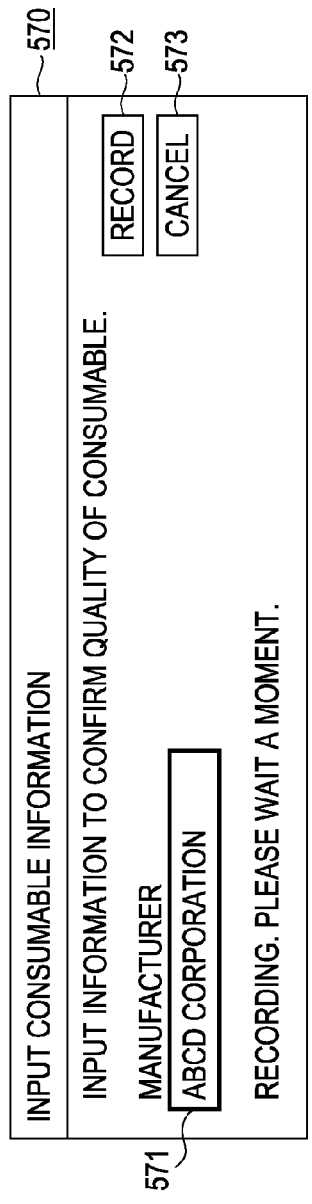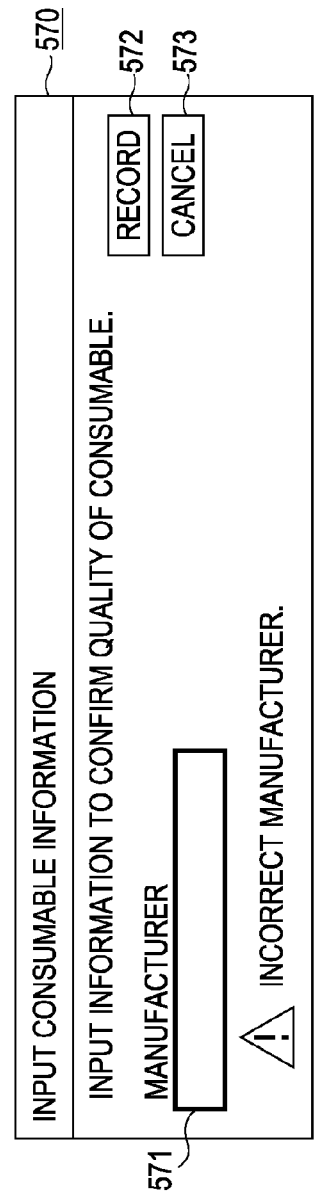

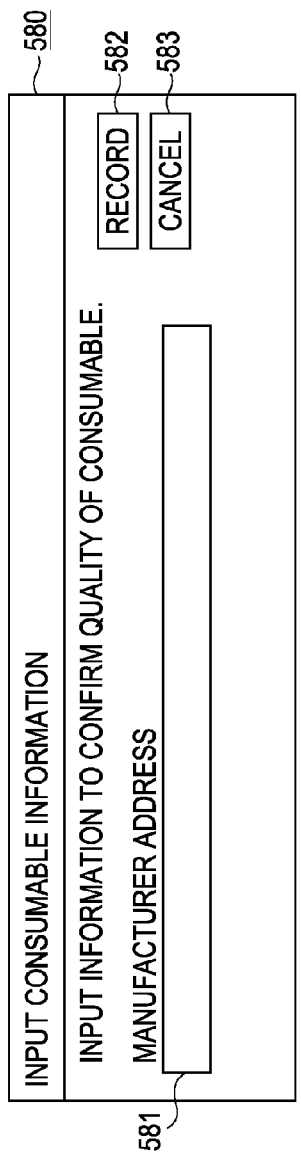
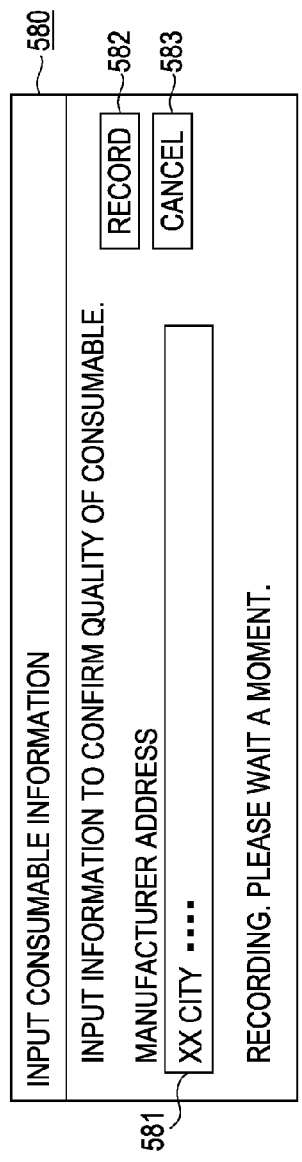
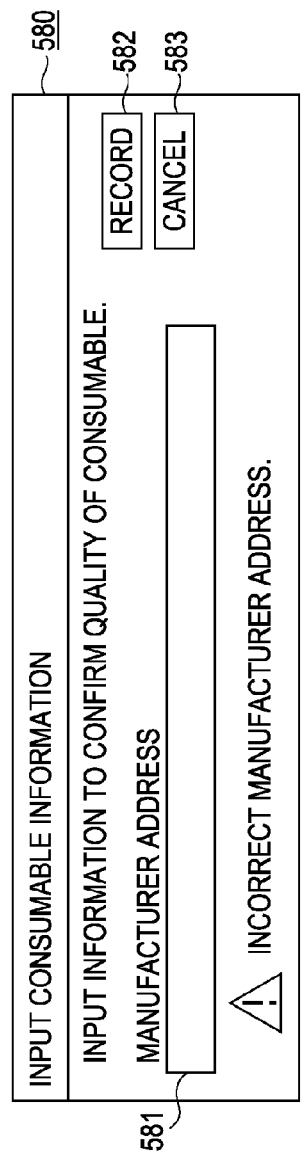

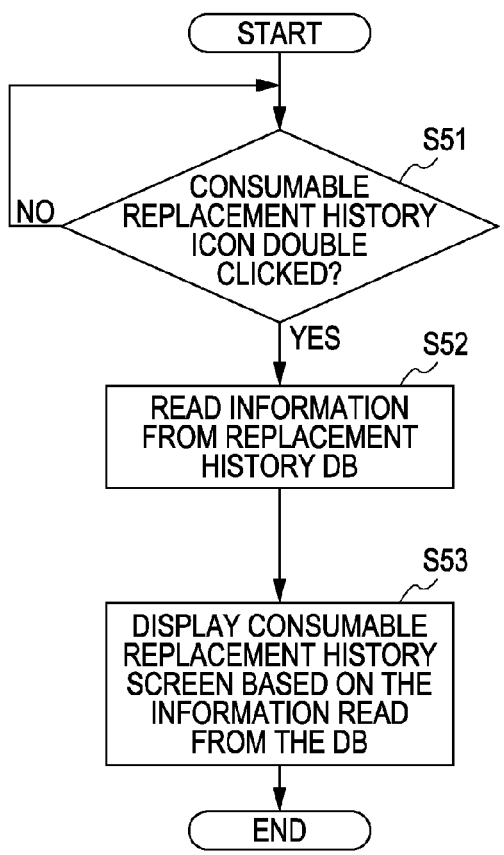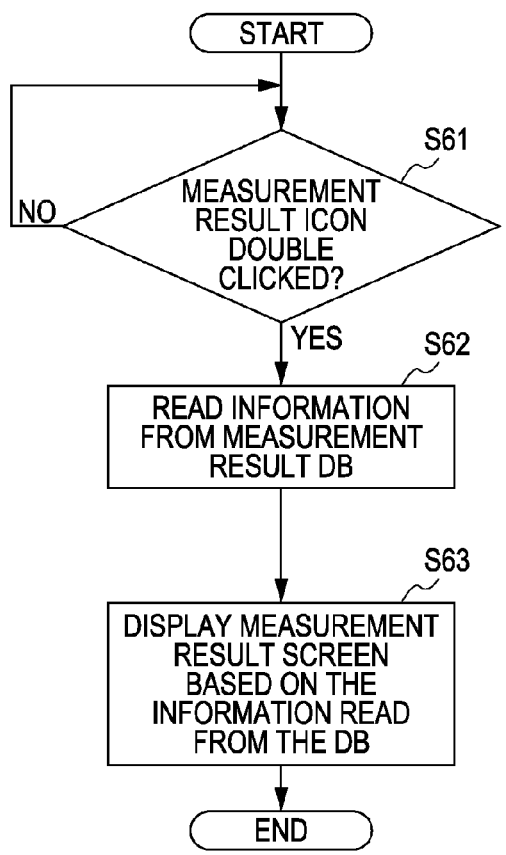
FIG. 20A
FIG. 20B

FIG. 21

| No. | DATE | TIME | LOGIN NAME | CONSUMABLE NAME | LOT No. | USE DATE | COMMENT |
|---|---|---|---|---|---|---|---|
| 10 | 2010/07/01 | 09:06:00 | max | DILUTION LIQUID A | A2010 | 2010/08/01 | UUU-900 ABCD CORPORATION XX CITY ..... |
| 9 | 2010/07/01 | 09:16:00 | max | STAIN LIQUID A | A2010 | 2010/08/01 | |
| 8 | 2010/07/01 | 09:26:00 | max | DILUTION LIQUID B | A2010 | 2010/08/01 | |
| 7 | 2010/07/01 | 09:36:00 | max | STAIN LIQUID B | A2010 | 2010/08/01 | |
| 6 | 2010/07/01 | 09:46:00 | max | SHEATH LIQUID | A2010 | 2010/08/01 | |
| 5 | 2010/07/04 | 09:06:00 | max | DILUTION LIQUID A | A2010 | 2010/08/01 | |
| 4 | 2010/07/04 | 09:16:00 | max | STAIN LIQUID A | A2010 | 2010/08/01 | |
| 3 | 2010/07/04 | 09:26:00 | max | DILUTION LIQUID B | A2010 | 2010/08/01 | |
| 2 | 2010/07/04 | 09:36:00 | max | STAIN LIQUID B | A2010 | 2010/08/01 | |
| 1 | 2010/07/04 | 09:46:00 | max | SHEATH LIQUID | A2010 | 2010/08/01 | |

FIG. 22

MEASUREMENT RESULTS

| SAMPLE No. | MEASUREMENT DATE | MEASUREMENT TIME | ... | ... | ... | ... |
|---|---|---|---|---|---|---|
| 0015 | 2010/06/11 | 10:22:09 | 0.3 | 1.7 | 3.6 | 0.00 |
| 0014 | 2010/06/11 | 10:20:04 | 0.1 | 1.0 | 0.0 | 0.00 |
| 0013 | 2010/06/11 | 10:18:24 | 30.2 | 29.5 | 4.9 | 2.00 |
| 0012 | 2010/06/11 | 10:14:08 | 40.2 | 38.1 | 70.1 | 3.28 |
| 0011 | 2010/06/11 | 09:58:02 | 0.1 | 1.0 | 0.0 | 0.00 |
| 0010 | 2010/06/11 | 09:50:22 | 0.3 | 1.0 | 0.0 | 0.00 |
| 0009 | 2010/06/11 | 09:40:21 | 0.2 | 1.0 | 0.2 | 0.00 |
| 0008 | 2010/06/11 | 09:30:20 | 0.1 | 1.0 | 0.0 | 0.00 |
| 0007 | 2010/06/11 | 09:26:48 | 0.1 | 1.0 | 0.4 | 0.00 |
| 0006 | 2010/06/10 | 22:00:54 | 38.4 | 30.7 | 2.7 | 4.85 |
| 0005 | 2010/06/10 | 21:27:31 | 0.1 | 1.1 | 0.3 | 0.12 |
| 0004 | 2010/06/10 | 21:14:22 | 0.2 | 1.1 | 0.1 | 0.12 |
| 0003 | 2010/06/10 | 21:14:03 | 0.1 | 1.0 | 0.0 | 0.00 |

ANALYZER AND METHOD OF ANALYZING

RELATED APPLICATIONS

This application is a continuation of, and claims the benefit of priority from, U.S. patent application Ser. No. 13/247,298, filed Sep. 28, 2011, which claims priority under 35 U.S.C. §119 to Japanese Patent Application No. 2010-219110 filed on Sep. 29, 2010, the entire content of which is hereby incorporated by reference.

FIELD OF THE INVENTION

The present invention relates to an analyzer which analyzes an analyte using a consumable together with the analyte and method of analyzing.

BACKGROUND ART

Various consumables are used for analyses in conventional analyzers which analyze samples, such as blood and urine of human or animal origin (hereinafter referred to as "analyte"). Examples of such consumables include analysis reagents which process analyte to a condition suited for analysis, washing reagent which is used to wash the analyzer at the start and end of an analysis operation, reactor vessels which are used to react the reagent and the sample, and disposable nozzles which are used to aspirate the sample. Predetermined quality and performance is expected of the consumables used in the analyzer. The analyzer can output accurate examination results insofar as the consumables used are of proper quality and within their expiration dates.

When the analyzer and the consumables are produced by the same manufacturer, the analyzer and the consumables can be fine tuned during parallel and simultaneous development so as to output optimally accurate analysis results when used together. When only the analyzer is developed anew so as to use conventional consumables, the analyzer may be fine tuned so as to output optimally accurate analysis results using the conventional consumables.

In this regard, Japanese Laid-Open Patent Publication No. 2007-333466 and Japanese Laid-Open Patent Publication No. 2003-248005, for example, disclose analyzers configured so that the analyzer records the information of the examination reagent to be used by reading an RFID tag or barcode adhered to the reagent container.

The conventional analyzers disclosed in Japanese Laid-Open Patent Publication No. 2007-333466 and Japanese Laid-Open Patent Publication No. 2003-248005 are not designed for use with the reagents that are unexpected by the manufacturer of the analyzer. Hence, when, for example, there is a mechanical blockage or problem with the analysis result, it is very difficult examine the cause of the problem despite claims from the operator or manager of the analyzer if the analysis operation has been performed using reagent from an unexpected manufacturer. Particularly in the case of analyzer which analyze clinical samples and requires a high degree of reliability concerning the analysis results, when an analysis result error does occur, it is extremely important to quickly examine the cause and prevent recurrence of the problem.

An object of the present invention is to eliminate these problems by providing an analyzer capable of suitably managing information of consumables even when a consumable is used which is unexpected by the manufacturer.

SUMMARY OF THE INVENTION

The scope of the present invention is defined solely by the appended claims, and is not affected to any degree by the statements within this summary.

According to a first aspect of the present invention, an analyzer which analyzes an analyte by using the analyte and consumables, the analyzer comprising: an automatic reading device which reads a first product information related to a consumable via an identifier given to the consumable or a container containing the consumable; and a controller which permits an analysis operation when the first product information is suitable information read by the automatic reading device via the identifier, and prompts an operator to manually enter a second product information comprising information specifying the manufacturer or seller of the consumable when the automatic reading device cannot read the identifier or the information read via the identifier is not suitable as the first product information and permits the analysis operation and storage of the input second product information when the operator has entered the second product information.

According to a second aspect of the present invention, a method of analyzing an analyte with an analyzer which uses consumables together with the analyte, the method comprising: reading a first product information related to a consumable via an identifier given to the consumable or a container containing the consumable; permitting an analysis operation by the analyzer when the information read via the identifier is suitable as the first product information; outputting information which prompts the operator to manually input a second product information that comprises information specifying the manufacturer or seller of the consumable when the identifier cannot be read or when the information read via the identifier is not suitable as the first product information; and storing the input second product information and permitting an analysis operation by the analyzer when the operator has input the second product information.

The effect or significance of the present invention will become clear from the following description of the embodiments. The embodiment described below is an illustration of the present invention and the invention is in no respect limited to the embodiment.

BRIEF DESCRIPTION OF THE DRAWINGS

FIG. 4 shows the structure of the information processing device of the embodiment;

FIG. 5 conceptually shows the replacement history database DB of the embodiment;

FIG. 10 is a flow chart showing the lot number input process of the embodiment;

FIGS. 13A, 13B, and 13C show the expiration date input dialogs of the embodiment;

FIGS. 15A, 15B, and 15C show the product code input dialogs of the embodiment;

FIGS. 17A, 17B, and 17C show the manufacturer input dialogs of the embodiment;

FIGS. 19A, 19B, and 19C show the manufacturer address input dialogs of the embodiment;

FIGS. 20A and 20B are flow charts showing the display processes of the consumable replacement history screen and the measurement result screen of the information processing device of the embodiment;

FIG. 21 shows the consumable replacement history screen of the embodiment; and

FIG. 22 shows the measurement result screen of the embodiment.

DETAILED DESCRIPTION OF THE PREFERRED EMBODIMENTS

The embodiment applies the present invention to a clinical sample analyzer which performs examinations of proteins and blood sugar samples (urine qualitative examinations), and examinations of red blood cells, white blood cells, and epithelial cells (urine sediment examinations). The examination of urine sediment is performed on samples that require results of urine qualitative analysis and urine sediment analysis. In this embodiment, a plurality of sample containers which contain different samples are placed in a sample rack, and the sample rack is placed in the sample analyzer that performs examinations of each sample.

An embodiment of the sample analyzer is described below with reference to the drawings.

Figure 1:
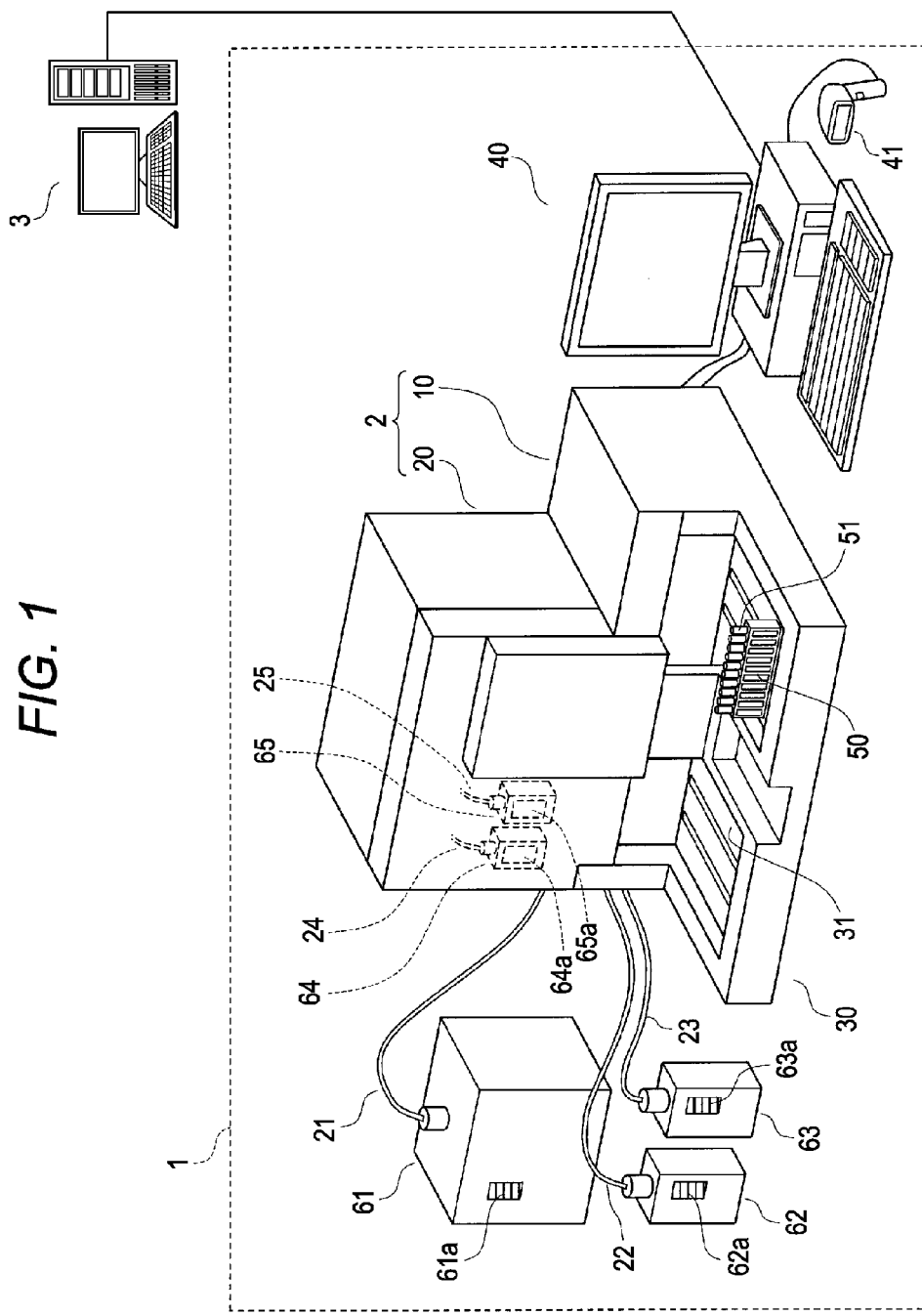
FIG. 1 shows the general structure of a system which includes the analyzer of the present invention.

FIG. 1 shows the general structure of a system that includes a sample analyzer 1. The sample analyzer 1 of the present embodiment has a measuring device 2, transport device 3, and information processing device 40.

The sample measuring device 2 has a first measuring unit 10 which performs quantitative urine examines, and a second measuring unit 20 which performs urine sediment examinations. The first measuring unit 10 and the second measuring unit 20 are mutually connected so as to be capable of communication. The first measuring unit 10 and the second measuring unit 20 are also respectively connected to the information processing device 40 so as to be capable of communication. The first measuring unit 10 is also connected to the transport device 30 so as to be capable of communication.

The second measuring unit 20 has tubes 21 through 25 as shown in the drawing. One end of the tubes 21 through 25 is connected to an aspiration section 203 (refer to FIG. 3) within the second measuring unit 20. The other end of the tubes 21 through 23 is connected to the reagent containers 61 through 63, respectively, outside the device, and the other end of tubes 24 and 24 is connected the reagent containers 64 and 65, respectively, inside the device. The reagent within the reagent containers 61 through 65 is aspirated the aspiration section 203 through the tubes 21 through 25, respectively, and subsequently used in the measurement processes of the second measuring unit 20.

The reagent containers 61 through 65 accommodate reagents (consumables) to be used in the measurements performed by the second measuring unit 20. When any of the reagents accommodated in the reagent containers 61 through 65 becomes depleted from the measurements performed by the second measuring unit 20, the operator can replace the depleted reagent container with a new reagent container. The reagent containers 61 through 65 each have a barcode label 61a through 65a respectively adhered thereon. A reagent code (product information) composed of several numbers is recorded in the barcode information of the barcode labels 61a through 65a.

The reagent code is described below referring to FIG. 2B.

The transport device 30 is a single unit used commonly by the first measuring unit 120 and the second measuring unit 20. The transport device 30 is installed on the front side of the sample measuring device 2, and is provided with a transport pass 31. The transport pass 31 has a bottom surface that is planar and lower in steps from the top surface of the transport device 30. A transport rack 50 which is transported on the transport pass 31 has ten holders capable of holding ten sample containers 51. The sample container 51 is transported on the transport pass 31 together with the sample rack 50 by being held in the holder of the sample rack 50. A barcode label (not shown in the drawing) identifying the sample is adhered to the side surface of the sample container 51.

The information processing device 40 is connected to a host computer 3 via a communication line so as to be capable of communication. The information processing device 40 is also connected to a barcode reader 41 which reads the reagent code of the barcode labels 61a through 65a adhered to the reagent containers 61 through 65.

The host computer 3 returns an order in response to an order query related to the measurement of the sample received from the information processing device 40. The host computer 3 determines the order of the second measuring unit 20 based on the analysis result received from the first measuring unit via the information processing device 40.

Figure 2A:
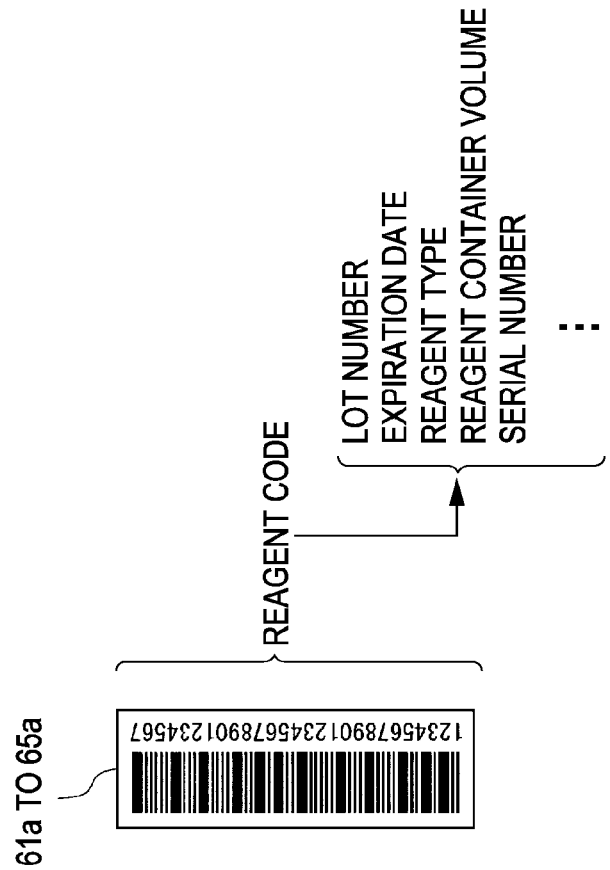
FIG. 2A shows a side view showing details of the reagent container and the second measuring unit of the embodiment.

FIG. 2A is a side view showing structural details of the second measuring unit 20 and the reagent containers 61 and 62.

A float sensor 26 is connected to the tip of the tube 21 which is connected to the reagent container 61. The float sensor 26 has a float 26a and a shaft 26b. The float 26a is configured so as to rise or fall along the shaft 26b in response to the liquid surface of the reagent within the reagent container 61. The shaft 26b has a hollow structure, and the bottom end of the shaft 26b is positioned near the bottom surface of the reagent container 61.

The float sensor 26 detects when the reagent is less than a predetermined amount by positioning the float 26a at a predetermined position. The detection signal of the float sensor 26 is output to a controller 201 (refer to FIG. 3) of the second measuring unit 20 via a cable disposed along the tube 21. The reagent within the reagent container 61 is aspirated through the shaft 26b and tube 26b by the aspirator 203 (refer to FIG. 3) of the second measuring unit 20. When replacing the reagent container 61, the tube 21 and the float sensor 26 are removed from the reagent container 61, then the tube 21 and the float sensor 26 are connected to a new reagent container 61.

The tip of the tube 22 which is connected to the reagent container 62 is drawn to the vicinity of the bottom surface of the reagent container 62. The tube 22 is provided with a prism sensor 22a in the interior of the second measuring unit 20. The prism sensor 22a is configured so as to detect bubbles within the tube 22. When the prism sensor 22a detects a bubble, it is understood that the reagent remaining within the reagent container 62 is less than the predetermined amount. The detection signal of the prism sensor 22a is output to the controller 201 of the second measuring unit 20. When replacing the reagent container 62, the tube 22 is removed from the reagent container 62, then the tube 22 is connected to a new reagent container 62. Note that the tubes 23 through 25 connected to the reagent containers 63 through 65 are also provided with prism sensors 23a through 25a, respectively, similar to the tube 22.

Figure 2B:
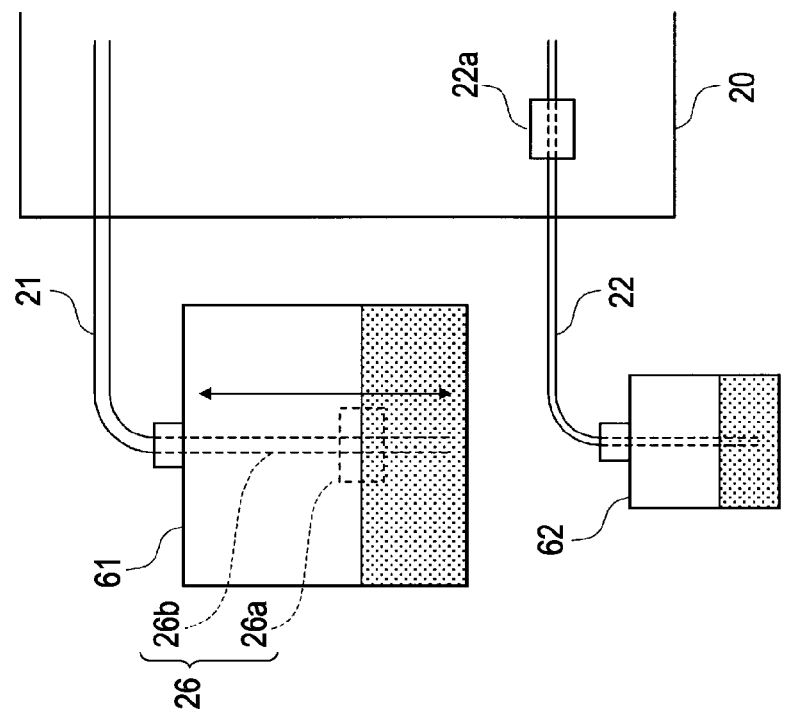
FIG. 2B shows the structure of the barcode label.

FIG. 2B shows the structure of the barcode labels 61a through 65a.

A reagent code composed of several numbers is recorded in the barcode information of the barcode labels 61a through 65a as mentioned above. Numbers corresponding to the stored reagent code are listed together in the barcode labels 61a through 65a as shown in the drawing.

The reagent code includes the lot number of the reagent, the expiration date of the reagent, type of reagent, volume of reagent, and serial number. Note that the reagent code does not include information specifying the manufacturer or seller.

The reagent code is unique information assigned to each reagent container and is composed of twenty or more numbers which the manufacturer of the sample analyzer 2 provides to the reagent container containing the reagent determined to be appropriate by pretesting. Therefore, it is extremely unlikely that barcode information will match a proper reagent code when the barcode label adhered to the reagent container contains reagent that is unexpected by the manufacturer of the sample analyzer 2.

Figure 3:
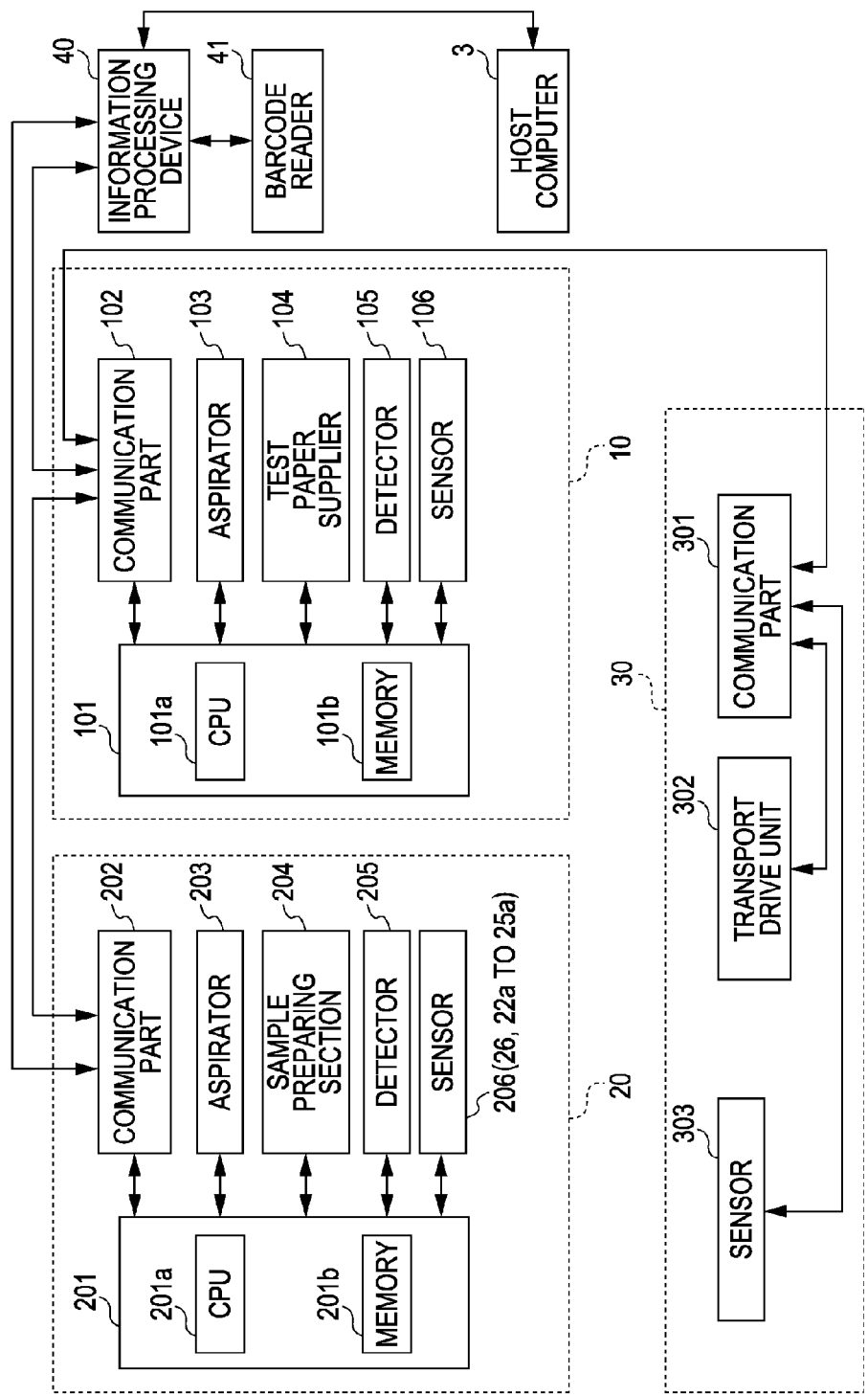
FIG. 3 shows the structures of the first measuring unit, second measuring unit, and transport device of the embodiment.

FIG. 3 shows the structures of the first measuring unit 10, second measuring unit 20, and transport device 30.

The first measuring unit 10 incorporates a controller 101, communication section 102, aspirator 103, test paper supplier 104, detector 105, and sensor 106.

The controller 101 has a CPU 101a and a memory 101b. The CPU 101a executes a computer program stored in the memory 101b to control the various parts of the first measuring unit 10. The CPU 101a also controls the parts of the transport device 30 via the communication section 102. The memory 101b has a memory means such as a RAM, ROM, hard disk or the like.

The communication section 102 processes the signals received from the controller 101, and outputs the processed signals to the second measuring unit 20, transport device 30, and the information processing device 40, and also processes the signals received from the second measuring unit 20, transport device 30, and the information processing device 40 and then outputs the processed signals to the controller 101. The aspirator 103 aspirates the sample in the sample container 51 positioned in front of the first measuring unit 10. The test paper supplier 104 takes a test paper required for measurement from the test paper feeder that stores the test paper, and drops a drip of sample aspirated by the aspirator 103 on the fed test paper. The detector 105 measures the test paper spotted with the sample. The measurement result obtained by the measurement is output to the controller 101 and analyzed by the CPU 101a.

The sensor 106 incorporates a sensor disposed on the first measuring unit 10, and a barcode reader which reads the sample number from the barcode label of the sample container 51 positioned in front of the first measuring unit 10. The output signal of the sensor 106 is output to the controller 101.

The second measuring unit 20 incorporates a controller 201, communication section 202, aspirator 203, sample preparing device 204, detector 205, and sensor 206.

The controller 201 has a CPU 201a and a memory 201b. The CPU 201a executes a computer program to control the various parts of the second measuring unit 20. The memory 201b has a memory means such as a RAM, ROM, hard disk or the like. The memory 201b stores the computer program executed by the CPU 201a. The memory 201b also stores the used amount of reagent in the reagent containers 61 through 65. The used amount of reagent in the reagent containers stored in the memory 201b is incremented in response to the use of the reagent and is reset when the reagent container is replaced. The memory 201b also stores the upper limit of the used amount of each reagent corresponding to the volumes of the reagent containers 61 through 65. When the used amount of reagent exceeds the upper limit of used reagent, it is determined that the reagent in the reagent container is less than the predetermined amount. Note that the used amount and upper limit of the reagent are stored in the memory 201b regardless of the power ON/OFF state of the second measuring unit 20.

The communication section 202 processes the signals received from the controller 201, and outputs the processed signals to the first measuring unit 10 and the information processing device 40, and also processes the signals received from the first measuring unit 10 and the information processing device 40 and then outputs the processed signals to the controller 201. The aspirator 203 aspirates the sample in the sample container 51 positioned in front of the second measuring unit 20, and aspirates the reagent in the reagent containers 61 through 65 through the tubes 21 through 25. The sample preparing device 204 mixes the sample aspirated by the aspirator 203 and the reagent required for measurement to prepare the measurement sample for the detector 205. The detector 205 measures the sample prepared by the sample preparing device 204. The measurement result obtained by this measurement is output to the controller 201.

The sensor 206 incorporates a float sensor 26 which detects when the reagent within the reagent container 61 is less than a predetermined amount, and prism sensors 22a through 25a which detect when the reagent within the reagent containers 62 through 65 is less than the predetermined amount. The output signal of the sensor 206 is output to the controller 201.

The transport device 30 has a communication section 301, transport drive section 302, and sensor 303. The communication section 301 processes the signals received from the first measuring unit 10, and outputs the processed signals to each part of the transport device 30, and also processes the signals received from each part of the transport device 30 and outputs the processed signals to the first measuring unit 10. The transport drive section 302 includes a mechanism which drives each part of the transport device 30, and is controlled by the CPU 101a of the first measuring unit 10. The sensor 303 includes various sensors of the transport device 30, and the output signals of the sensor 303 are output to the first measuring unit 10 through the communication section 301. The transport drive section 302 is controlled by control signals received from the controller 101 of the first measuring unit 10 through the communication section 301.

FIG. 4 shows the structure of the information processing device 40.

The information processing device 40 is a personal computer configured by a body 400, input section 410, and displays part 420. The body 400 has a CPU 401, ROM 402, RAM 403, hard disk 404, reading device 405, I/O interface 406, image output interface 407, and communication interface 408.

The CPU 401 executes a computer program stored in the ROM 402, and a computer program loaded in the RAM 403. The CPU 401 also queries the host computer 3 based on the order queries received from the first measuring unit 10 and the second measuring unit 20. The CPU 401 also transmits the orders received from the host computer 3 to the first measuring unit 10 and the second measuring unit 20.

The RAM 403 is used when reading the computer programs stored in the ROM 402 and hard disk 404. The RAM 403 is used as the work area of the CPU 401 when the CPU 401 executes the computer programs.

Various computer programs executed by the CPU 401, such as an operating system and application programs, as well as the data used in the execution of these computer programs are installed on the hard disk 404. That is, the computer program which displays information on the display part 420 based on the analysis result received from the first measuring unit 10, and the program which displays information on the display part 420 based on the analysis result received from the second measuring unit 20 are installed on the hard disk 404. The hard disk 404 also stores the replacement history DB, and the measurement results DB. The measurement results received from the second measuring unit 420 are sequentially written to the measurement result DB. The replacement history DB is described later with reference to FIG. 5.

The reading device 405 is configured by a CD drive or DVD drive or the like, and is capable of reading computer programs and data stored on recording media. The I/O interface 406 is connected to the input section 410 which includes a mouse and keyboard, and inputs data to the information processing device 40 when the operator uses the input section 410. The image output interface 407 is connected to the display part 420 which incorporates a display or the like, and outputs image signals corresponding to the image data to the display part 420. The display part 420 displays images based on the received image signals. The communication interface 408 transmits and receives data to/from the first measuring unit 10, second measuring unit 20, and host computer 3.

FIG. 5 conceptually shows and example of the replacement history DB stored on the hard disk 404 of the information processing device 40. When the operator replaces one of the reagent containers 61 through 65, the information regarding the replaced reagent container is added to the replacement history DB.

The replacement history DB includes the replacement date, replacement time, login name, type of consumable, lot number, expiration date, product code, manufacturer, and manufacturer address.

The time and date on which the reagent container was replaced are respectively stored in the replacement time and replacement date items. The name of the operator using the information processing device 40 when the reagent replacement was performed is stored in the login name item. The type of reagent container replaced is stored in the type of consumable item. Note that "sheath liquid," "dilution liquid B," "dilution liquid A"," "stain liquid B," and "stain liquid A" are the reagents respectively accommodated in the reagent containers 61 through 65.

The reagent lot number and expiration date are stored in the lot number and expiration date items. The reagent product code or product name is stored in the product code item. The reagent manufacturer or seller is stored in the manufacturer item. The reagent manufacturer address or seller address is stored in the manufacturer address item.

Figure 6:
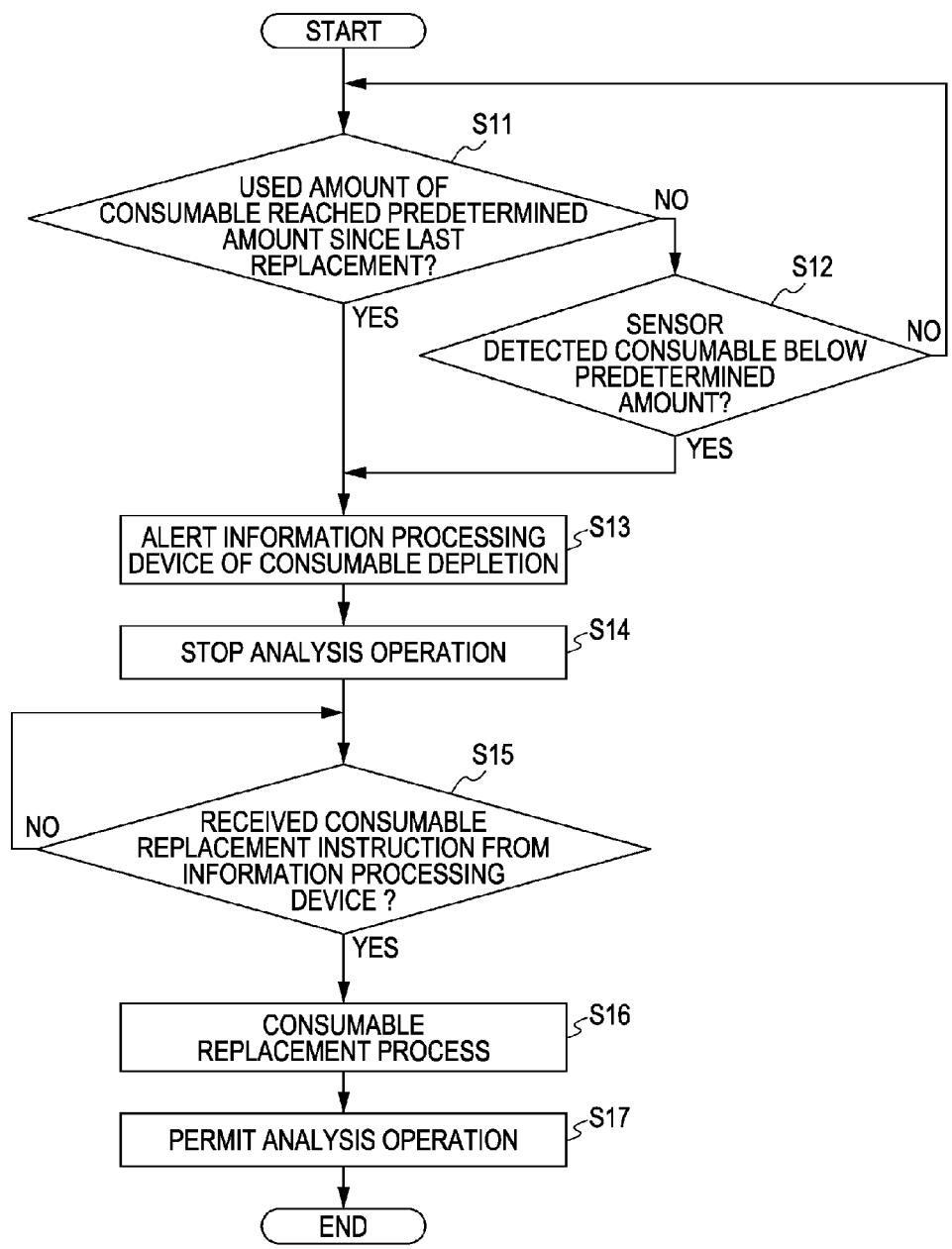
FIG. 6 is a flow chart showing the consumable replenishment process.

FIG. 6 is a flow chart showing the consumable replenishment process of the second measuring unit 20.

The CPU 201a of the second measuring unit 20 determines whether the used amount of reagent (consumable) within the respective reagent containers 61 through 65 since the last respective replacement has reached the predetermined amount (upper limit of the used amount of reagent) set for each reagent container based on the used amount of reagent (S11). Note that the used amount of reagent and the upper limit of the used amount of reagent are stored in the memory 201b (refer to FIG. 2).

When the CPU 201a determines that the used amount of reagent from any reagent container has reached the predetermined amount since the last replacement (S11: YES), the process moves to S13. When the CPU 201a determines that the used amount of reagent from any reagent container has not reached the predetermined amount since the last replacement (S11: NO), the CPU 201a determines whether the sensor 206 (float sensor 26, prism sensors 22a through 25a) has detected whether any reagent within the reagent containers 61 through 65 is less than the predetermined amount (S12). When no reagent is less than the predetermined amount (S12: NO), the process returns to S11. When any reagent is less than the predetermined amount and consumable depletion is detected (S12: YES), the process advances to S13.

The CPU 201a then alerts the information processing device 40 that consumable depletion has occurred for the reagent container depletion determined YES in S11 or the reagent container depletion determined YES in S12 (S13). The CPU 201a then stops the analysis operation of the second measuring unit 20 (S14). That is, the CPU 201a suspends any more aspiration from the sample container 51 by the second measuring unit 20, and completes the processing of the already aspirated sample from the sample container 51 by the second measuring unit 20.

When the consumable depletion alert is received from the second measuring unit 20, the information processing device 40 prompts the operator to replace the consumable and the operator then replaces the consumable. Thereafter, the information processing device 40 transmits the consumable replacement instruction to the second measuring unit 20. The consumable replacement process performed in the information processing device 40 when the consumable depletion alert has been received in S13 is described below with reference to FIG. 7.

When the consumable replacement instruction is received from the information processing device 40 (S15: YES), the CPU 201a of the second measuring unit 20 performs the consumable replacement process (S16). That is, predetermined amounts of the reagent within the reagent containers 61 through 65 is aspirated to the chambers in the second measuring unit 20 via the tubes 21 through 25. Thereafter, the CPU 201a permits the analysis operation (S17). In this way, the aspiration of new sample from the sample container 51 is permitted. Then the consumable replenishment process by the second measuring unit 20 is completed.

Figure 7:
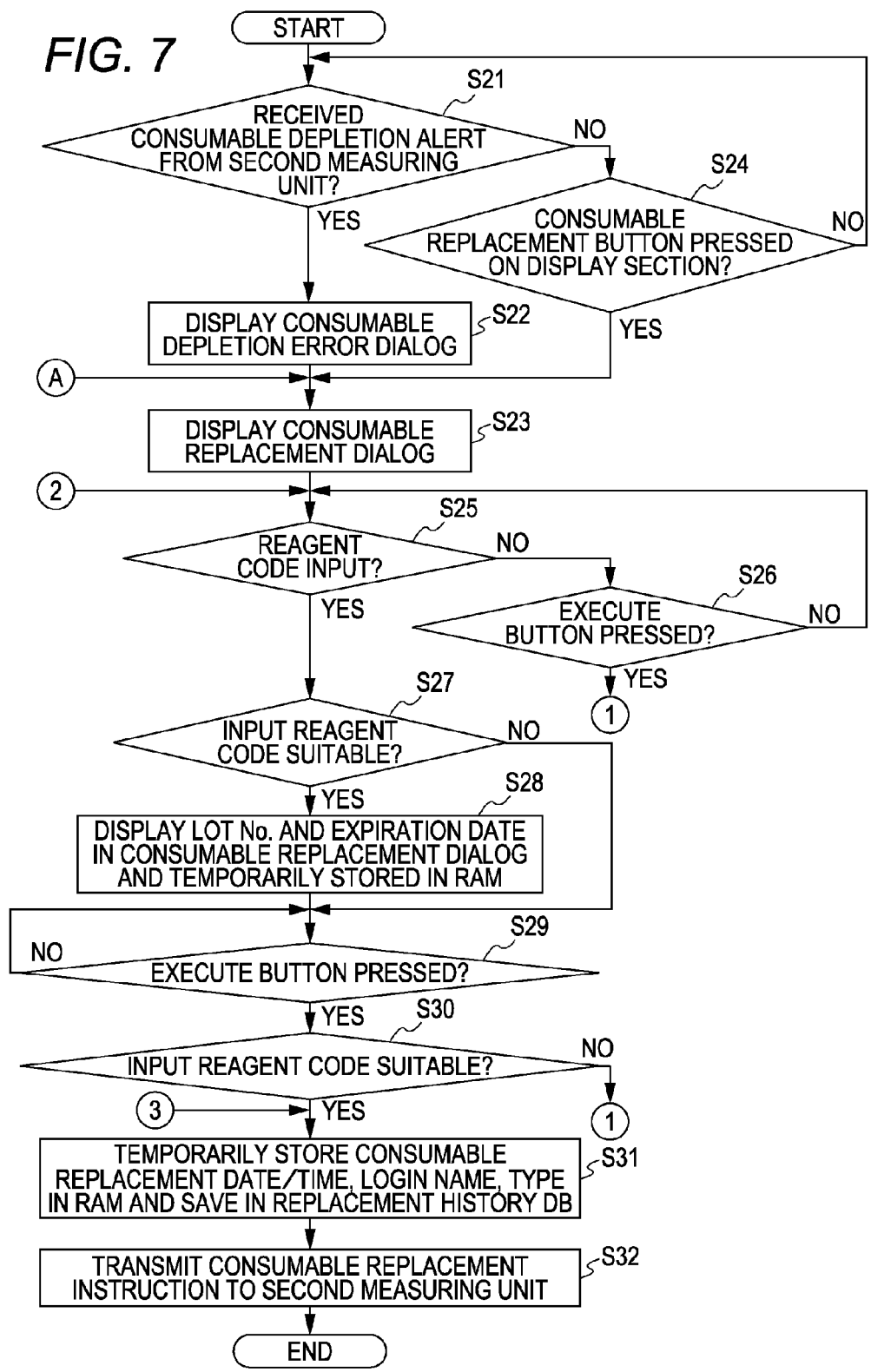
FIG. 7 is a flow chart showing the consumable replacement process of the information processing device of the embodiment.

FIG. 7 is a flow chart showing the consumable replacement process by the information processing device 40.

When the consumable depletion alert is received from the second measuring unit 20 (S21: YES), the CPU 401 of the information processing device 40 displays a consumable depletion error dialog 510 on the display part 420 (S22).

Figure 9A:
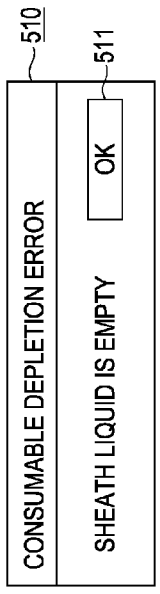
FIG. 9A shows consumable depletion error dialog of the embodiment.

FIG. 9A shows the consumable depletion error dialog 510 displayed on the display part 420. The consumable depletion dialog 510 has an OK button 511. The identity of the depleted reagent container is displayed on the consumable depletion error dialog 510 as shown in the drawing.

Returning now to FIG. 7, when the OK button 511 is pressed on the consumable depletion error dialog 510, the CPU 401 of the information processing device 40 displays the consumable replacement dialog 520 on the display part 420 (S23). The CPU 401 displays the consumable replacement dialog 520 on the display part 420 when the operator presses a consumable replacement button (not shown in the drawing) (S23) even when a consumable depletion alert has not been received (S21: NO). Note that without receiving a consumable depletion alert (S21: NO), the process returns to S21 when the consumable replacement button is not pressed (S24: NO). When the consumable replacement dialog 520 is displayed (S23), the operator replaces the reagent container.

Figure 9B:
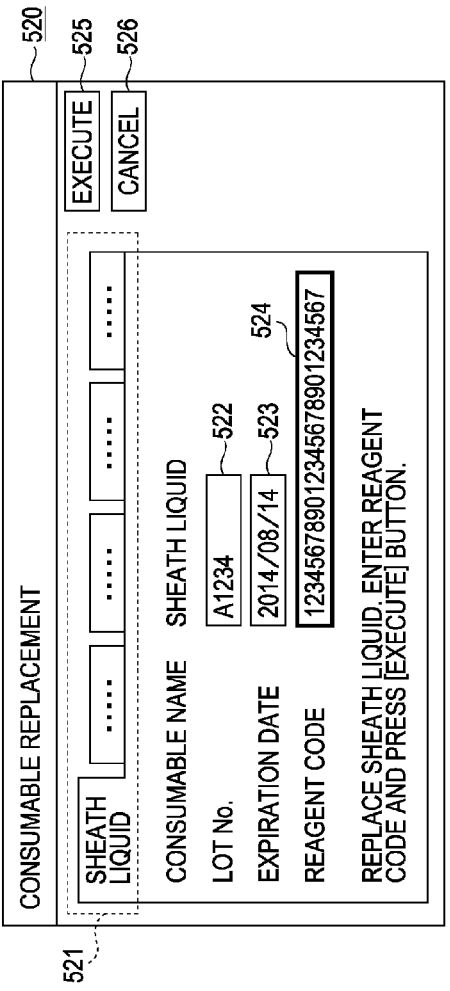
FIG. 9B shows consumable replacement dialog.

FIG. 9B shows the consumable replacement dialog 520 displayed on the display part 420. The consumable replacement dialog 520 has a tag field 521, lot number display field 522, expiration date display field 523, reagent code input field 524, execute button 525, and cancel button 526.

When a tag in which the name of the reagent has been written is pressed in the tag field 521, a screen is displayed which allows the reagent code of this reagent to be entered. FIG. 9B shows an example of an input screen for "sheath liquid" (reagent contained in the reagent container 61). Note that when the OK button 511 is pressed in the consumable depletion error dialog 510, the consumable replacement dialog 510 is displayed and the reagent input screen shown in the consumable depletion error dialog 510 is automatically displayed.

The lot number and expiration date are automatically displayed in the lot number display field 522 and the expiration date display field 523, respectively, when a suitable reagent code is entered in the reagent code input field 524 as will be described later.

The reagent code entry is performed by the operator using the barcode reader 41 to read the barcode information on the barcode label adhered to the replaced reagent container. Note that the reagent code entry may also be accomplished by the operator directly inputting the characters written on the barcode label via the input section 410 (refer to FIG. 4).

When the operator pressed the execute button 525, a predetermined process is executed as will be described later. When the operator presses the cancel button 526, the process returns to S22 when the determination of S21 is YES in FIG. 7, and the process returns to S21 when the determination of S24 is YES in FIG. 7.

Returning now to FIG. 7, when the consumable replacement dialog 520 is displayed (S23), the CPU 401 of the information processing device 40 determines that the reagent code has been entered in the reagent code input field 524 (S25). When the reagent code is entered (S25: YES), the process advances to S27.

When the reagent code is not entered (S25: NO), the CPU 401 determines whether the execute button 525 has been pressed in the consumable replacement dialog 520 (S26). When the execute button 525 is pressed (S25: YES), the process advances to S33 of FIG. 8 via the connector 1. When the execute button 525 is not pressed (S26: NO), the process returns to S25.

In S27, the CPU 401 determines whether the input reagent code is suitable. When the reagent code is suitable, it means that use of the reagent is expected or guaranteed by the analyzer manufacturer. When the reagent code is unsuitable, it means that use of the reagent is unexpected or not guaranteed by the analyzer manufacturer. Whether the reagent code is suitable is determined by whether the character array entered in the reagent code input field 524 has a predetermined format. For example, the reagent code may include a checksum, so that appropriateness of the format can be determined by checking the checksum generated from the reagent code against a checksum included in the reagent code. Note that barcode information matching the reagent code is never included in the barcode adhered to the reagent container which is unexpected by the manufacturer of the sample measuring device 2 as previously described. Therefore, the determination of reagent code suitability is limited to cases in which the reagent code has been entered based on the barcode label of the reagent container expected by the manufacturer of the sample measuring device 2.

When the input reagent code is suitable (S27: YES), the CPU 401 displays the lot number and expiration date obtained from the input reagent code in the lot number display field 522 and the expiration date display field 523, respectively, of the consumable replacement dialog 520, and temporarily stores the lot number and the expiration date in the RAM 403 (refer to FIG. 4) (S28). When the reagent code is unsuitable (S27: NO), the process moves to S29.

When the execute button 520 is then pressed on the consumable replacement dialog 520 (S29: YES), the CPU 401 determines whether the input reagent code is suitable (S30). When the input reagent code is unsuitable (S30: NO), the process moves to S33 of FIG. 8 via the connector 1. On the other hand, when the input reagent code is suitable (S30: YES), the date and time the consumable was replaced, the operator login name at that time, the type of reagent replaced, and the information temporarily stored in the RAM 403 are stored in the replacement history DB (S31). Thus, the replacement of the reagent container 61 is saved in the replacement history DB shown in FIG. 5.

Note that the type of consumable stored in the replacement history DB is the reagent in the tag field 521 selected in the consumable replacement dialog 520. The lot number and the expiration date saved in the replacement history DB are temporarily stored in the RAM 403 when the execute button 525 is pressed. When the reagent code is suitable, the product code, manufacturer, and manufacturer address items in the replacement history DB are empty.

The CPU 401 transmits the consumable replacement instruction to the second measuring unit 20 (S32). The consumable replacement process ends when the input reagent code is suitable.

Figure 8:
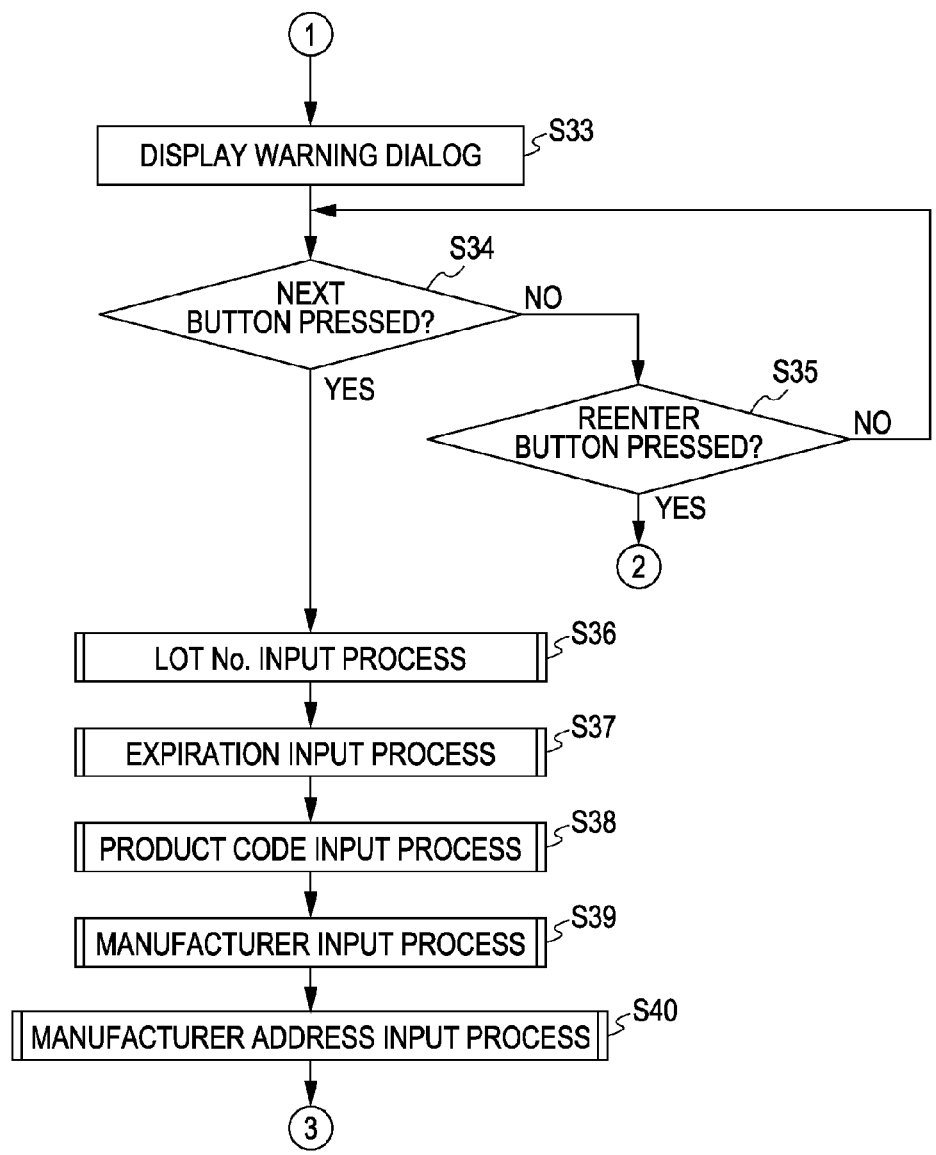
FIG. 8 is a flow chart showing the consumable replacement process of the information processing device of the embodiment.

FIG. 8 is a flow chart showing the consumable replacement process by the information processing device 40. This flow chart is executed when the determination of S26 is YES in FIG. 7, and when the determination of S30 is NO in FIG. 7.

The CPU 401 of the information processing device 40 displays the warning dialog 530 on the display section 420 (S33).

Figure 9C:
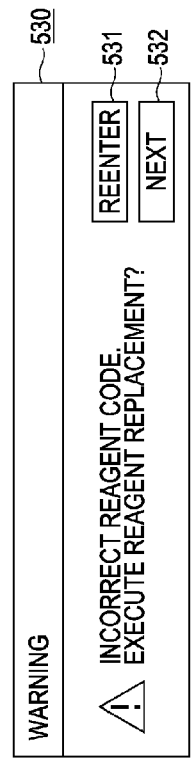
FIG. 9C shows a warning dialog.

FIG. 9C shows the warning dialog 530 displayed on the display part 420. The warning dialog 530 has a reenter button 531 and a NEXT button 532. The warning content is displayed in the warning dialog 530 as shown in the drawing.

Returning now to FIG. 8, the CPU 401 of the information processing device 40 changes the process in response to the button of the warning dialog 530 pressed by the operator. That is, when the NEXT button 532 is pressed (S34: YES), the process moves to S36. When the reenter button 531 is pressed (S34: NO, S35: YES), the process returns to S25 of FIG. 7 via the connector 2, and prompts for the reagent code to be reentered. When neither the reenter button 531 nor the NEXT button 532 have been pressed (S34: NO, S35: NO), the process enters standby until either button is pressed.

When the NEXT button 531 is pressed (S34: YES), the CPU 401 performs the lot number input process (S36), expiration date input process (S37), product code input process (S38), manufacturer input process (S39), and manufacturer address input process (S40). The process then moves to S31 of FIG. 7 via the connector 3. The lot number input process, expiration date input process, product code input process, manufacturer input process, and manufacturer address input process are described below with reference to FIGS. 10, 12, 14, 16, and 18.

FIG. 10 is a flow chart showing the lot number input process.

The CPU 401 of the information processing device 40 displays the lot number input dialog 540 on the display section 420 (S361) and receives the lot number input (S362).

Figure 11A:
FIGS. 11A, 11B, and 11C show the lot number input dialogs of the embodiment.
Figure 11B:
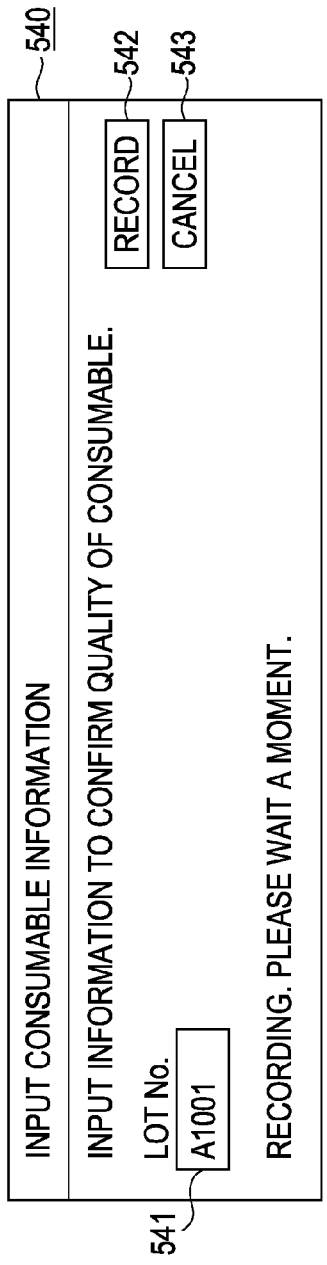
Figure 11C:
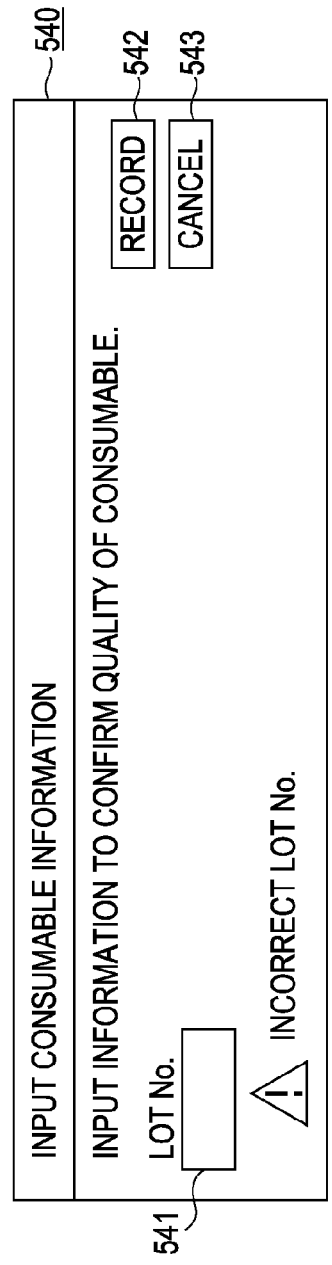

FIGS. 11A through 11C show the lot number input dialog 540 displayed on the display section 420. The lot number input dialog 540 has a lot number input field 541, record button 542, and cancel button 543. The operator manually inputs the lot number in the lot number input field 541 via the input section 410. The operator manually inputs the lot number given to the reagent container after the replacement.

Returning now to FIG. 10, the CPU 401 of the information processing device 40 changes the process in response to the button of the lot number input dialog 540 pressed by the operator. That is, when the record button 542 is pressed (S363: YES), the process moves to S365. When the cancel button 543 is pressed (S363: NO, S364: YES), the lot number dialog 540 is closed, and the process returns to S23 of FIG. 7 via the connector A. When neither the record button 542 nor the cancel button 543 have been pressed (S363: NO, S364: NO), the process enters standby until either button is pressed.

When the record button 542 is pressed (S363: YES), the CPU 401 displays the following message: "Recording. Please wait a moment." on the lot number input dialog 540 (S365) as shown in FIG. 11(*b*). After the process of S365, the CPU 401 determines whether the cancel button 543 has been pressed within 10 seconds (S366). In this way, the operator has a 10 second grace period to make corrections. When the cancel button 543 is pressed within 10 seconds (S366: YES), the process returns to S362, and the CPU 401 receives the reentered lot number input. On the other hand, when the cancel button 543 is not pressed within 10 seconds (S366: NO), the CPU 401 determines whether the input lot number is suitable (S367). Whether the lot number is suitable is determined by, for example, the number of characters of the lot number.

When the input lot number is unsuitable (S367: NO), the CPU 401 displays the message: "Incorrect lot number." on the lot number input dialog 540 (S368) and the process returns to S362 as shown in FIG. 11(*c*). On the other hand, when a suitable lot number is input (S367: YES), the CPU 401 temporarily stores the input lot number in the RAM 403 (S369). Then the lot number input process ends.

Figure 12:
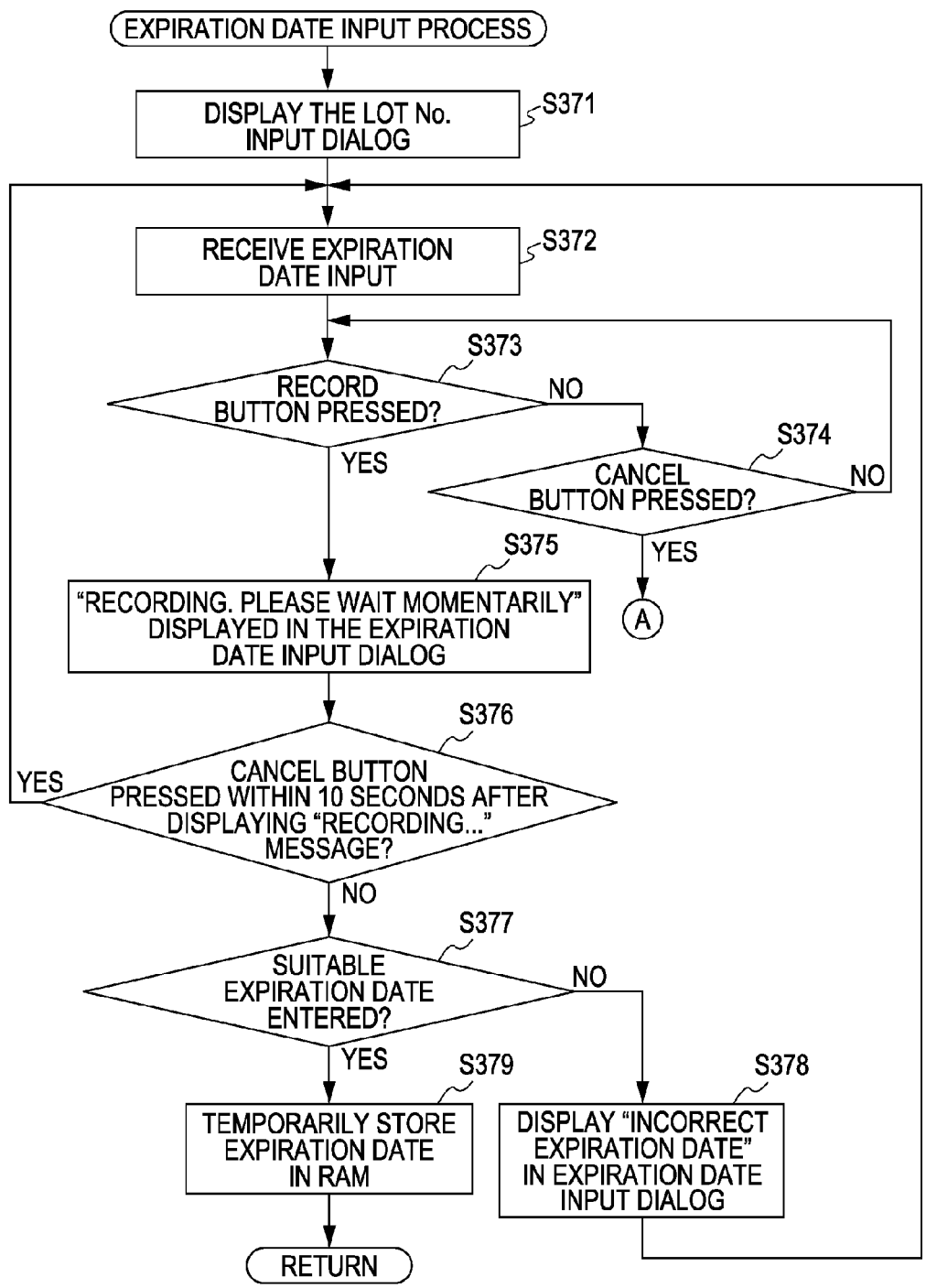
FIG. 12 is a flow chart showing the expiration date input process of the embodiment.

FIG. 12 is a flow chart showing the expiration date input process.

The CPU 401 of the information processing device 40 displays the expiration date input dialog 550 on the display section 420 (S371), and receives the input of the expiration date (S372).

FIGS. 13A through 13C show the expiration date input dialog 550 displayed on the display section 420. The expiration date input dialog 550 has an expiration date input field 551, record button 552, and cancel button 553. The operator can manually enter the expiration date in the expiration date input field 551 via the input section 410. The operator manually inputs the expiration date given to the reagent container after the replacement.

Returning now to FIG. 12, the CPU 401 of the information processing device 40 changes the process in response to the button of the expiration date input dialog 550 pressed by the operator. That is, when the record button 552 is pressed (S373: YES), the process moves to S375. When the cancel button 553 is pressed (S373: NO, S374: YES), the expiration date input dialog 550 is closed, and the process returns to S23 of FIG. 7 via the connector A. When neither the record button 552 nor the cancel button 553 have been pressed (S373: NO, S374: NO), the process enters standby until either button is pressed.

When the record button 552 is pressed (S373: YES), the CPU 401 displays the following message: "Recording. Please wait a moment." on the expiration date input dialog 550 (S375) as shown in FIG. 13(*b*). After the process of S375, the CPU 401 determines whether the cancel button 553 has been pressed within 10 seconds (S376). In this way the operator has a 10 second grace period to make corrections. When the cancel button 553 is pressed within 10 seconds (S376: YES), the process returns to S372, and the CPU 401 receives the reentered expiration date input. On the other hand, when the cancel button 553 is not pressed within 10 seconds (S366: NO), the CPU 401 determines whether the input expiration date is suitable (S377). Whether the expiration date is suitable is determined by, for example, the format of the expiration date.

When the input expiration date is unsuitable (S377: NO), the CPU 401 display the message: "Incorrect expiration date." on the expiration date input dialog 550 (S378) and the process returns to S372 as shown in FIG. 13(*c*). On the other hand, when a suitable expiration date is input (S377: YES), the CPU 401 temporarily stores the input expiration date in the RAM 403 (S379). Thus, the expiration date input process ends.

Figure 14:
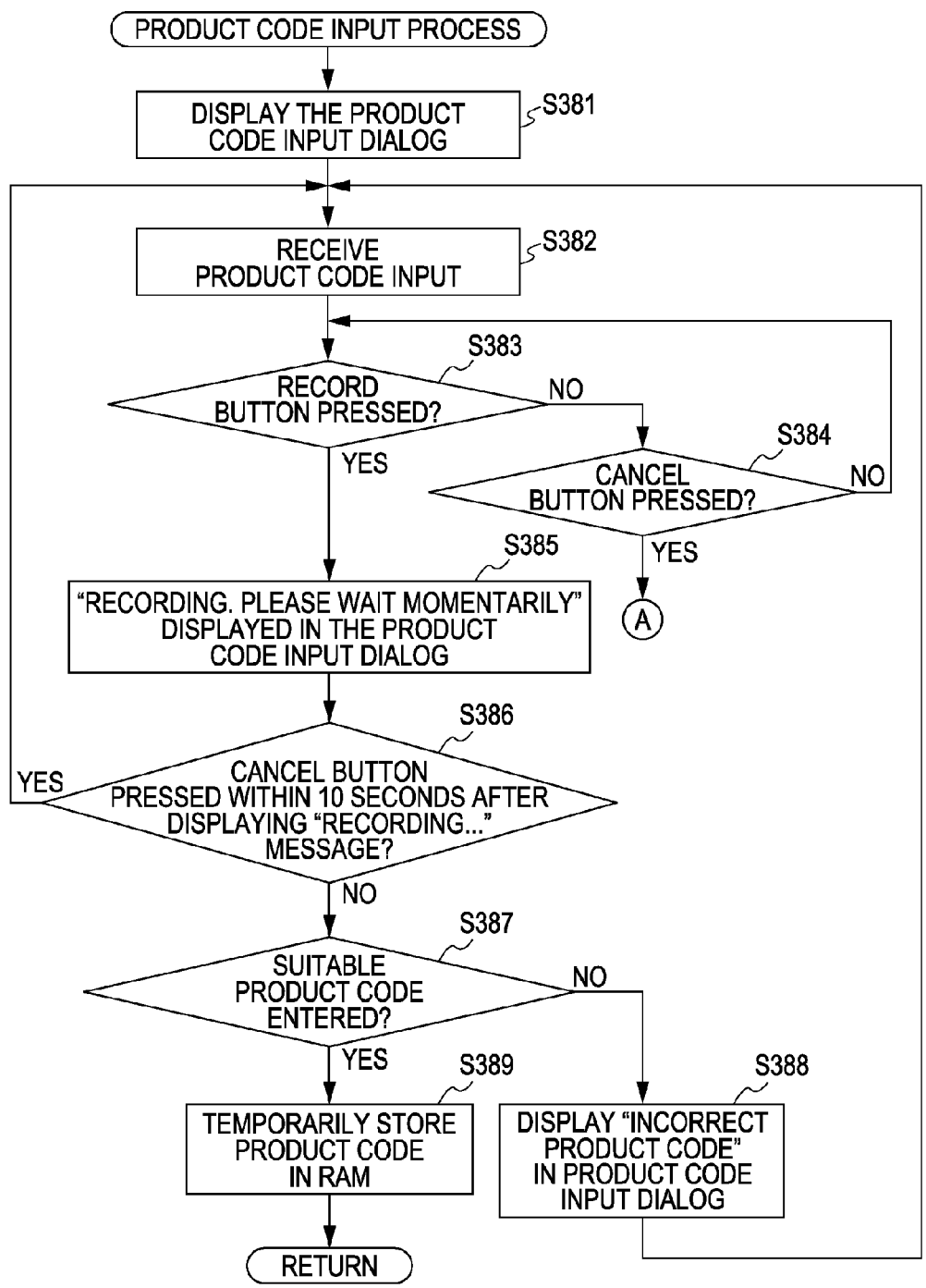
FIG. 14 is a flow chart showing the product code input process of the embodiment.

FIG. 14 is a flow chart showing the product code input process.

The CPU 401 of the information processing device 40 displays the product code input dialog 560 on the display section 420 (S381), and receives the input product code (S382).

FIGS. 15A through 15C show the product code input dialog 560 displayed on the display section 420. The product code input dialog 560 has a product code input field 561, record button 562, and cancel button 563. The operator manually enters the product code or product name in the product code input field 561 via the input section 410. The operator manually enters the product code or product name given on the reagent container after replacement.

Returning now to FIG. 14, the CPU 401 of the information processing device 40 changes the process in response to the button of the produce coder input dialog 560 pressed by the operator. That is, when the record button 562 is pressed (S383: YES), the process moves to S385. When the cancel button 563 is pressed (S383: NO, S384: YES), the product code dialog 560 is closed, and the process returns to S23 of FIG. 7 via the connector A. When neither the record button 562 nor the cancel button 563 have been pressed (S383: NO, S384: NO), the process enters standby until either button is pressed.

When the record button 562 is pressed (S383: YES), the CPU 401 displays the following message: "Recording. Please wait a moment." on the produce code input dialog 560 (S385) as shown in FIG. 15(*b*). After the process of S385, the CPU 401 determines whether the cancel button 563 has been pressed within 10 seconds (S386). In this way the operator has a 10 second grace period to make corrections. When the cancel button 563 is pressed within 10 seconds (S386: YES), the process returns to S382, and the CPU 401 receives the reentered produce code input. On the other hand, when the cancel button 563 is not pressed within 10 seconds (S386: NO), the CPU 401 determines whether the input produce code is suitable (S387). Whether the entered product code is suitable is determined by, for example, the number of characters of the product code.

When the input product code is unsuitable (S387: NO), the CPU 401 displays the message: "Incorrect product code." on the product code input dialog 560 (S388) and the process returns to S382 as shown in FIG. 15(c). On the other hand, when a suitable product code is input (S387: YES), the CPU 401 temporarily stores the input product code in the RAM 403 (S389). Thus, the product code input process ends.

Figure 16:
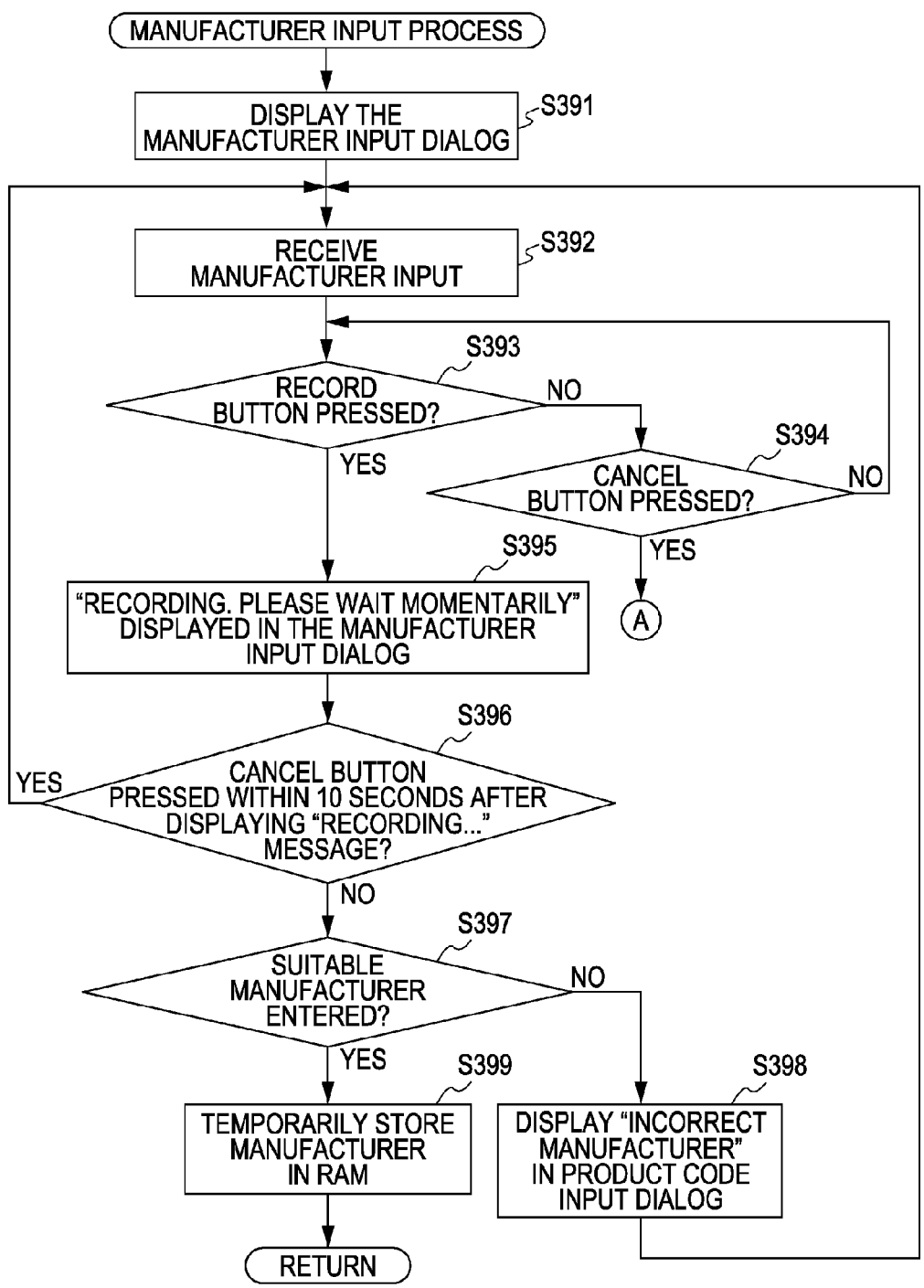
FIG. 16 is a flow chart showing the manufacturer input process of the embodiment.

FIG. 16 is a flow chart showing the manufacturer input process.

The CPU 401 of the information processing device 40 displays the manufacturer input dialog 570 on the display section 420 (S391), and receives the input of the manufacturer (S392).

FIGS. 17A through 17C show the manufacturer input dialog 570 displayed on the display section 420. The manufacturer input dialog 570 has a manufacturer input field 571, record button 572, and cancel button 573. The operator manually enters the manufacturer or seller in the manufacturer input field 571 via the input section 410. The operator manually enters the manufacturer or seller given on the reagent container after replacement.

Returning now to FIG. 16, the CPU 401 of the information processing device 40 changes the process in response to the button of the manufacturer input dialog 570 pressed by the operator. That is, when the record button 572 is pressed (S393: YES), the process moves to S395. When the cancel button 573 is pressed (S393: NO, S394: YES), the manufacturer dialog 570 is closed, and the process returns to S23 of FIG. 7 via the connector A. When neither the record button 572 nor the cancel button 573 have been pressed (S393: NO, S394: NO), the process enters standby until either button is pressed.

When the record button 572 is pressed (S393: YES), the CPU 401 displays the following message: "Recording. Please wait a moment." on the manufacturer input dialog 570 (S395) as shown in FIG. 17(b). After the process of S395, the CPU 401 determines whether the cancel button 573 has been pressed within 10 seconds (S396). In this way the operator has a 10 second grace period to make corrections. When the cancel button 573 is pressed within 10 seconds (S396: YES), the process returns to S392, and the CPU 401 receives the reentered manufacturer input. On the other hand, when the cancel button 573 is not pressed within 10 seconds (S396: NO), the CPU 401 determines whether the input manufacturer is suitable (S397). Whether the manufacturer is suitable is determined by, for example, the number of characters of the manufacturer.

When the input manufacturer is unsuitable (S397: NO), the CPU 401 display the message: "Incorrect manufacturer." on the manufacturer input dialog 570 (S398) and the process returns to S392 as shown in FIG. 17(c). On the other hand, when a suitable manufacturer is input (S397: YES), the CPU 401 temporarily stores the input manufacturer in the RAM 403 (S399). Thus, the manufacturer input process ends.

Figure 18:
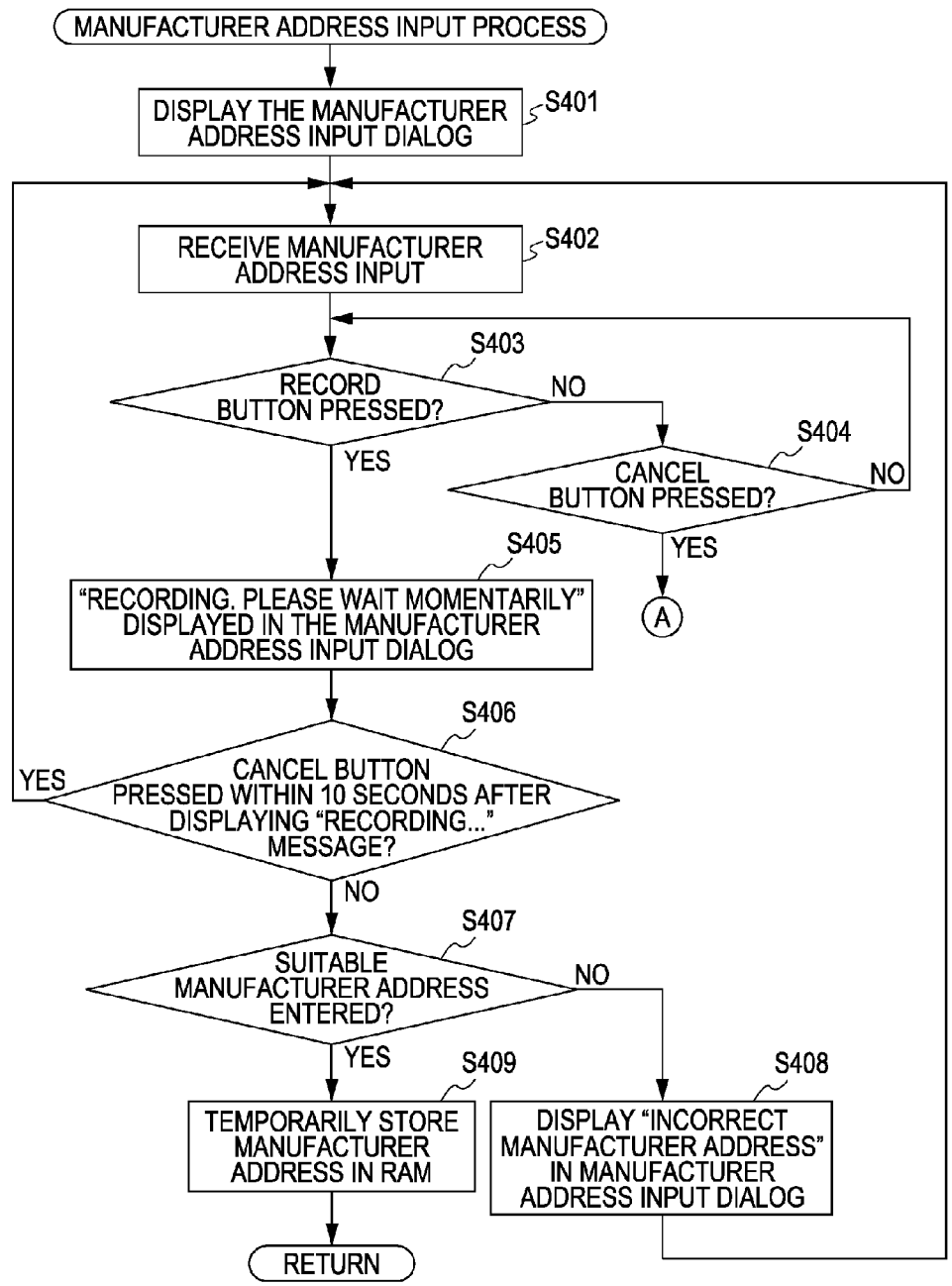
FIG. 18 is a flow chart showing the manufacturer address input process of the embodiment.

FIG. 18 is a flow chart showing the manufacturer address input process.

The CPU 401 of the information processing device 40 displays the manufacturer address input dialog 580 on the display section 420 (S401), and receives the input of the manufacturer address (S402).

FIGS. 19A through 19C show the manufacturer address input dialog 580 displayed on the display section 420. The manufacturer address input dialog 580 has a manufacturer address input field 581, record button 582, and cancel button 583. The operator manually enters the manufacturer address or seller address in the manufacturer address input field 581 via the input section 410. The operator manually enters the manufacturer address or seller address given on the reagent container after replacement.

Returning now to FIG. 18, the CPU 401 of the information processing device 40 changes the process in response to the button of the manufacturer address input dialog 580 pressed by the operator. That is, when the record button 582 is pressed (S403: YES), the process moves to S405. When the cancel button 583 is pressed (S403: NO, S404: YES), the manufacturer address input dialog 580 is closed, and the process returns to S23 of FIG. 7 via the connector A. When neither the record button 582 nor the cancel button 583 has been pressed (S403: NO, S404: NO), the process enters standby until either button is pressed.

When the record button 582 is pressed (S403: YES), the CPU 401 displays the following message: "Recording. Please wait a moment." on the manufacturer address input dialog 580 (S405) as shown in FIG. 19(b). After the process of S405, the CPU 401 determines whether the cancel button 583 has been pressed within 10 seconds (S406). In this way the operator has a 10 second grace period to make corrections. When the cancel button 583 is pressed within 10 seconds (S406: YES), the process returns to S402, and the CPU 401 receives the reentered manufacturer address input. On the other hand, when the cancel button 583 is not pressed within 10 seconds (S406: NO), the CPU 401 determines whether the input manufacturer address is suitable (S407). Whether the manufacturer is suitable is determined by, for example, the number of characters of the manufacturer address.

When the input manufacturer address is unsuitable (S407: NO), the CPU 401 display the message: "Incorrect manufacturer." on the manufacturer address input dialog 580 (S408) and the process returns to S402 as shown in FIG. 19(c). On the other hand, when a suitable manufacturer address is input (S407: YES), the CPU 401 temporarily stores the input manufacturer address in the RAM 403 (S409). Thus, the manufacturer address input process ends.

In this way, the lot number input process, expiration date input process, product code input process, manufacturer input process, and manufacturer address input process are sequentially executed, then the process moves to S31 of FIG. 7 via the connector 3 as shown in FIG. 8. In this case, the information temporarily stored in the RAM 403 includes the lot number, expiration date, product code, manufacturer, and manufacturer address. Hence, unlike when the reagent code is suitable, the product information, product code, manufacturer, and manufacturer address are stored in the replacement history DB via the processes of S31 as shown in the upper level of FIG. 5. That is, it is understood that the operator entered the lot number, expiration date, product code, manufacturer and manufacturer address since the reagent code is unsuitable when the product code, manufacturer code, and manufacturer address items are empty in the replacement history DB.

FIG. 20A is a flow chart showing the display process of the consumable replacement history screen by the information processing device 40.

When the CPU 401 of the information processing device 40 determines that the consumable replacement history icon (not shown in the drawing) displayed in the display section 420 has been double clicked (S51: YES), the information of the replacement history DB is read from the hard disk 404 (S52). Specifically, the replacement date, replacement time, login name, type of consumable, lot number, expiration date, product code, manufacturer, and manufacturer address are read from the replacement history DB. The CPU 401 then displays the consumable replacement history screen 61 on the display section 420 based on the information read in S52 (S53).

FIG. 21 shows the consumable replacement history screen 610 displayed on the display part 420. The consumable replacement history screen 610 has a display region 611, and the information from the replacement history DB is displayed in the display region 611.

The numbers in the display region 611 are numbers corresponding to the data from the replacement history DB. The date, time, login name, name of consumable, lot number, and use period in the display region 611 represent the replacement date, replacement time, login name, type of consumable, lot number and expiration date from the replacement history DB.

The comment field of the display region 611 displays the text strings linked to the product code, manufacturer, and manufacturer address of the replacement history DB. For example, when the upper level of the replacement history DB of FIG. 5 is displayed in the display region 611, the display shows the linked string of "UUU-900" for the product code, "ABCD Corporation" for the manufacturer, and "XX City" for the manufacturer address as shown in FIG. 21. Note that the comment field is not editable by the operator.

When the comment field is empty, it is understood that the reagent code has been determined to be suitable, that is, use of the reagent is guaranteed or expected by the manufacturer of the analyzer; whereas when the comment field is not empty, it is understood that the reagent has not been determined to be suitable, that is, the use of the reagent is not guaranteed or expected by the manufacturer of the analyzer.

FIG. 20B is a flow chart showing the display process of the measurement result screen by the information processing device 40.

When the CPU 401 of the information processing device 40 determines that the measurement result icon (not shown in the drawing) displayed in the display section 420 has been double clicked (S61: YES), the information of the measurement result DB is read from the hard disk 404 (S62). The CPU 401 then displays the measurement result screen 620 on the display section 420 based on the information read in S62 (S63).

FIG. 22 shows the measurement result screen 620 displayed on the display part 420. The measurement result screen 620 has a display region 621, and the information from the measurement result DB is displayed in the display region 621.

The sample number which identifies the sample is displayed in the sample number field of the display region 621. The time and date on which the measurement was performed by the second measuring unit 20 are displayed in the measurement time and measurement date fields in the display region 621. The measurement results are displayed in other fields.

When the consumable replacement history screen 610 is displayed as described above, the measurements of each sample can be known by referencing the display region 621. In the measurements of the each sample, it can also be known at what time the reagent container used was replaced by referencing the measurement result screen 620 of FIG. 22.

According to the present embodiment, when an error occurs in the measurement result of a sample, the reagent used in the measurement of that sample can be specified by referencing the measurement time and date (measurement date and measurement time) in the measurement result screen 620 of FIG. 22, and the replacement time and date (date and time) in the consumable replacement history screen 610 of FIG. 21. Hence, the reagent used for measurement at the time an error occurs can be specified by referring to the reagent replacement date and time in the consumable replacement history screen 610 of FIG. 21 and the date and time of the error when an error has occurred during the operation of the sample measuring device 2. Whether the reagent used at such a time is unexpected or not guaranteed by the manufacturer of the sample measuring device 2 can also be comprehended by referencing the comment field in the consumable replacement history screen 610 of FIG. 21. Moreover, information related to the composition of the reagent used can be obtained easily since the information specifying the manufacturer or seller of the reagent is displayed in the comment field of the consumable replacement history screen 610. Thus, since specified reagent and reagent container can be examined as a source of the problem in such a case, it is possible to narrow down the source of the problem.

According to the present embodiment, in the lot number input process, expiration date input process, product code input process, manufacturer input process, and manufacturer address input process, the operator can correct the input content by pressing the cancel button within 10 seconds even after the input content has been recorded. Hence, the operator can correct the input content when the operator suspects an error in the input content.

According to the present embodiment, in the lot number input process, expiration date input process, product code input process, manufacturer input process, and manufacturer address input process, the operator can return to the process of S23 of FIG. 7 by pressing the cancel button when receiving the input content. Hence, when the process unintentionally advances to S36 of FIG. 8, for example when there is an error in the reagent code input, or the wrong reagent is entered in the reagent comment, the operator can reenter the reagent comment. The operator can also start other work immediately since the input operation is terminated and the input screen is closed even during the input of the lot number in S36 through S40 of FIG. 8.

According to the present embodiment, when a reagent code is entered in the reagent code input field of the consumable replacement dialog 520 using a barcode reader 41, the process does not advance immediately to S33 of FIG. 8 when barcode reader 41 cannot read the barcode information or the read barcode information is an unsuitable reagent code. Hence, the operator can reenter the number on the barcode label via the input section 410 even when the barcode label is soiled. When, for example, a barcode label is read for a reagent container that is unexpected by the manufacturer of the sample measuring device 2, the operator can replace the reagent container with a reagent container that is expected by the manufacturer of the sample measuring device 2 and then the barcode reader 41 can read the barcode label.

According to the present embodiment, the operator can enter the number of the barcode label via the input section 410 into the reagent comment input field of the consumable replacement dialog 520. Hence, the consumable replacement process can be performed without problem even when the barcode reader 41 malfunctions.

Although the present invention has been described by way of an embodiment, the invention is not limited to this embodiment.

For example, although the embodiment is described in terms of urine as the measurement object, blood may also be the measurement object. That is, the present invention may be applied to a clinical sample analyzer which analyzes blood, and the present invention may also be applied to a clinical sample analyzer which examines other clinical sampler such as interstitial tissue. The measurement object samples may be collected from humans or may be collected from animals.

Although the operator enters the lot number and the like from the input section 410 in the processes of S36 through S40 of FIG. 8 in the above embodiment, the present invention is not limited to this configuration inasmuch as the sample analyzer 1 may be provided with a digital camera to allow the input of a package photo of the reagent container photographed by the digital camera. In this case, whether the reagent container is expected by the manufacturer of the analyzer can be determined by presence or absence of a package photo of the reagent container.

Although common information (lot number and expiration date) is included in the information input in the processes of S36 through S40 with the information included in the reagent code in the above embodiment, the present invention is not limited to this configuration inasmuch as the information included in the reagent code may be completely different or completely identical to the information input in the processes of S36 through S40 of FIG. 8.

Although the reagent code is written on the barcode labels 61a through 65a to identify the reagent container in the above embodiment, the present invention is not limited to this configuration inasmuch as an RFID (radio frequency identification) tag may also be used. In this case, the reagent code is read using an RFID antenna rather than a barcode reader 41.

In the above embodiment, the float sensor 26 and prism sensors 22a through 25a detect when the reagent within the reagent containers 61 through 65 is less than a predetermined amount. However, the present invention is not limited to this configuration inasmuch as a float sensor capable of detecting the residual amount of reagent may be disposed at the tip of the tubes 21 through 25 which are connected to the reagent containers. In this case, an amount of reagent less than the predetermined amount in the reagent containers 61 through 65 can be detected since the residual amount of reagent within the reagent containers 61 through 65 is detectable.

Although barcode labels 61a through 65a are adhered to the reagent containers 61 through 65, respectively, which contain reagent (consumable) in the above embodiment, the present invention is not limited to this configuration inasmuch as the barcode information may be provided directly on the consumable such as test paper when a test paper or the like is used as a consumable for measurements.

Although reagent and test paper are used as consumables in the above embodiment, other examples of usable consumables include disposable nozzles which aspirate sample, and reactor containers (cuvettes) which contain the sample and reagent for reaction.

In the above embodiment, a barcode label bearing the reagent code is adhered to the reagent containers 61 through 65 which contain the reagent to be used by the second measuring unit 20. However, the present invention is not limited to this configuration inasmuch as a barcode label bearing the reagent code also may be adhered to the container containing the test paper used in the measurements performed by the first measuring unit 10. In this case, when replacing the test papers, the barcode information of the container holding the test papers is read by the barcode reader 41 in a process identical to that of the above embodiment. Similarly, a barcode label adhered to packing material may also be read by the barcode reader 41 in a process identical to that described above even when the barcode bearing the reagent code is adhered to the packaging of the reagent container containing the reagent.

The embodiment of the present invention may be variously modified insofar as such modification is within the scope of the art described in the claims.

What is claimed is:

1. An analyzer which analyzes an analyte by using the analyte and consumables, the analyzer comprising:
   a memory which stores replacement history of the consumables;
   an automatic reading device which reads a first product information related to a consumable via an identifier given to the consumable or a container containing the consumable; and
   a controller which permits an analysis operation when the first product information is suitable information read by the automatic reading device via the identifier, and prompts an operator to manually enter a second product information comprising information specifying the manufacturer or seller of the consumable when the automatic reading device cannot read the identifier or the information read via the identifier is not suitable as the first product information and permits the analysis operation when the operator has entered the second product information, wherein
   the memory stores the input information specifying the manufacturer or seller of the consumable when the operator has entered the second product information; and
   the memory does not stores the information specifying the manufacturer or seller of the consumable when the first product information is suitable information read by the automatic reading device via the identifier.

2. The analyzer of claim 1, further comprising
   a detecting device which detects a residual amount of consumable;
   wherein the detection device stops the operation of the analyzer when an insufficient residual amount of consumable is detected, and restarts the operation of the analyzer when the controller gives permission.

3. The analyzer of claim 1, further comprising
   a display part;
   wherein the second product information comprises a plurality of types of information; and
   the controller displays on the display part a first input screen image for receiving input of a first type of information when receiving the second product information, and displays on the display part a second input screen image for receiving input of a second type of information when information input is received via the first input screen image and the received information is suitable.

4. The analyzer of claim 3, wherein
   the first and second input screen images comprise a record key which records the received information, and a cancel key which cancels the reception of the information; and
   the controller activates the cancel key for a predetermined time after the information has been received on the first and second input screen images and the record key has been selected.

5. The analyzer of claim 3, wherein
   the controller receives a suspension of manual input of the second product information even if either the first or second input screen image is displayed.

6. The analyzer of claim 1, wherein
   the memory stores a result of the analysis of the analyte together with information indicating a time of the analysis and when the operator manually enters the second product information, the controller stores the input second product information together with the information indicating a time the consumable was replaced.

7. The analyzer of claim 1, wherein
the controller receives from the operator a selection to replace the consumable or re-input of the first product information when the automatic reading device cannot read the identifier or when the information read via the identifier is not suitable as the first product information, and prompts the operator to manually enter the second product information when replacement of the consumable has been selected.

8. The analyzer of claim 1, further comprising an input section;
wherein the consumable or the container holding the consumable is given a third product information similar to the first product information included in the identifier so that the third product information is visible for the operator; and
wherein the controller permits the analysis operation when the operator properly enters the third product information via the input section.

9. The analyzer of claim 1, wherein
the first product information is information that does not include information specifying the manufacturer or seller of the consumable.

10. The analyzer of claim 1, wherein
the first product information is unique information assigned to each individual consumable.

11. The analyzer of claim 1, wherein
the controller determines whether the first product information has a predetermined format, and, based on the determination result, determines whether the information read via the identifier is suitable as the first product information.

12. The analyzer of claim 1, wherein
the analyte is at least any one of blood, urine, and interstitial fluid.

13. The analyzer of claim 1, wherein
the consumable is at least any one of a reagent, test paper, reactor vessel, and a disposable.

14. The analyzer of claim 1, wherein
the identifier is at least any one of a barcode, and a RFID tag.

15. The analyzer of claim 1, wherein
the consumable is a reagent or test paper;
the automatic reading device is a barcode reader; and the identifier is a barcode, and
the barcode is adhered to a container containing the reagent or the test paper.

16. The analyzer of claim 1, wherein
the consumable is a test paper;
the automatic reading device is a barcode reader; and
the identifier is a barcode, and the barcode is adhered to the test paper.

17. The analyzer of claim 1, wherein
when the operator inputs second product information, the controller determines whether the second input product information is suitable, and the memory stores the input second product information when suitable second product information has been input.

18. The analyzer of claim 17, wherein
the second product information comprises as least one of the load number, product code, manufacturer, expiration date, and manufacturer address.

19. The analyzer of claim 17, wherein
the controller determines whether the second input product information the operator has input is suitable by the number of characters input by the operator.

20. A method of analyzing an analyte with an analyzer which uses consumables together with the analyte, the method comprising:
reading a first product information related to a consumable via an identifier given to the consumable or a container containing the consumable;
permitting an analysis operation by the analyzer when the information read via the identifier is suitable as the first product information;
outputting information which prompts the operator to manually input a second product information that comprises information specifying the manufacturer or seller of the consumable when the identifier cannot be read or when the information read via the identifier is not suitable as the first product information; and
storing the input information specifying the manufacturer or seller of the consumable in a memory and permitting an analysis operation by the analyzer when the operator has input the second product information, wherein
the memory does not stores the information specifying the manufacturer or seller of the consumable when the first product information is suitable information read by the automatic reading device via the identifier.

* * * * *